US011298538B2

(12) United States Patent
Huertas Fernandez et al.

(10) Patent No.: US 11,298,538 B2
(45) Date of Patent: Apr. 12, 2022

(54) NEUROMODULATION CALIBRATION BASED ON NEUROPHYSIOLOGICAL SIGNALS

(71) Applicant: Boston Scientific Neuromodulation Corporation, Valencia, CA (US)

(72) Inventors: Ismael Huertas Fernandez, Madrid (ES); Que T. Doan, West Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 83 days.

(21) Appl. No.: 16/454,864

(22) Filed: Jun. 27, 2019

(65) Prior Publication Data

US 2020/0001086 A1 Jan. 2, 2020

Related U.S. Application Data

(60) Provisional application No. 62/691,962, filed on Jun. 29, 2018.

(51) Int. Cl.
*A61N 1/36* (2006.01)
*A61N 1/372* (2006.01)
(Continued)

(52) U.S. Cl.
CPC .......... *A61N 1/36062* (2017.08); *A61B 5/377* (2021.01); *A61B 5/389* (2021.01);
(Continued)

(58) Field of Classification Search
CPC .............. A61N 1/0551; A61N 1/36062; A61N 1/36139; A61N 1/36146; A61N 1/37247; A61N 1/377; A61B 5/0484; A61B 5/0488
See application file for complete search history.

(56) References Cited

U.S. PATENT DOCUMENTS

2005/0222626 A1\* 10/2005 DiLorenzo ........... A61N 1/3605
607/2
2010/0305660 A1\* 12/2010 Hegi .................. A61N 1/36071
607/60
(Continued)

FOREIGN PATENT DOCUMENTS

WO WO-2016090420 A1 \* 6/2016 ........... A61N 1/3614

OTHER PUBLICATIONS

Falowski, Steven M., "An Observational Case Series of Spinal Cord Stimulation Waveforms Visualized on Intraoperative Neuromonitoring", Neuromodulation: Technology at the Neural Interface, (onlinelibrary.wiley.com) DOI: 10.1111/ner.12781, www.neuromodulationjournal.com, pp. 1-10, 2018.

*Primary Examiner* — Carl H Layno
*Assistant Examiner* — Anh-Khoa N Dinh
(74) *Attorney, Agent, or Firm* — Schwegman Lundberg & Woessner, P.A.

(57) ABSTRACT

A system may include at least one sensor configured to bilaterally sense neurophysiological signals from the patient to provide bilateral sensing data, and at least one processor configured to calibrate at least a first electrode contact and a second electrode contact on the least one neuromodulation lead, including: instruct the neuromodulation device to deliver neuromodulation energy using at least the first electrode contact to cause a first neurophysiological response and at least the second electrode contact to cause a second neurophysiological response; receive from the at least one sensor first bilateral sensed data corresponding to the first neurophysiological response and second bilateral sensed data corresponding to the second neurophysiological response; and determine based on the first and second neurophysiological responses at least one of: physiological (Continued)

midline information or electrode-tissue coupling information.

20 Claims, 22 Drawing Sheets

(51) Int. Cl.
*A61N 1/05* (2006.01)
*A61B 5/377* (2021.01)
*A61B 5/389* (2021.01)

(52) U.S. Cl.
CPC ....... *A61N 1/0551* (2013.01); *A61N 1/36139* (2013.01); *A61N 1/36146* (2013.01); *A61N 1/37247* (2013.01)

(56) References Cited

U.S. PATENT DOCUMENTS

| | | | | |
|---|---|---|---|---|
| 2012/0277833 A1* | 11/2012 | Gerber | ................. | A61N 1/0526 607/62 |
| 2013/0245722 A1* | 9/2013 | Ternes | ................. | A61B 5/1107 607/62 |
| 2015/0127062 A1* | 5/2015 | Holley | ............... | A61N 1/36132 607/46 |
| 2016/0045751 A1* | 2/2016 | Jiang | .................... | A61B 5/0492 607/59 |
| 2016/0175586 A1* | 6/2016 | Edgerton | ........... | A61N 1/36185 604/20 |
| 2017/0281958 A1* | 10/2017 | Serrano Carmona | ........................ | A61N 1/37247 |

* cited by examiner

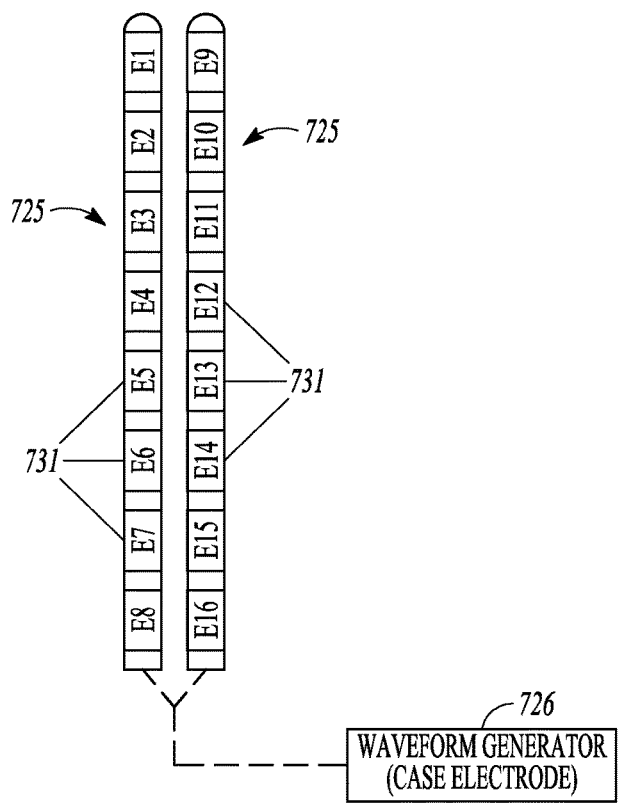
*FIG. 7*
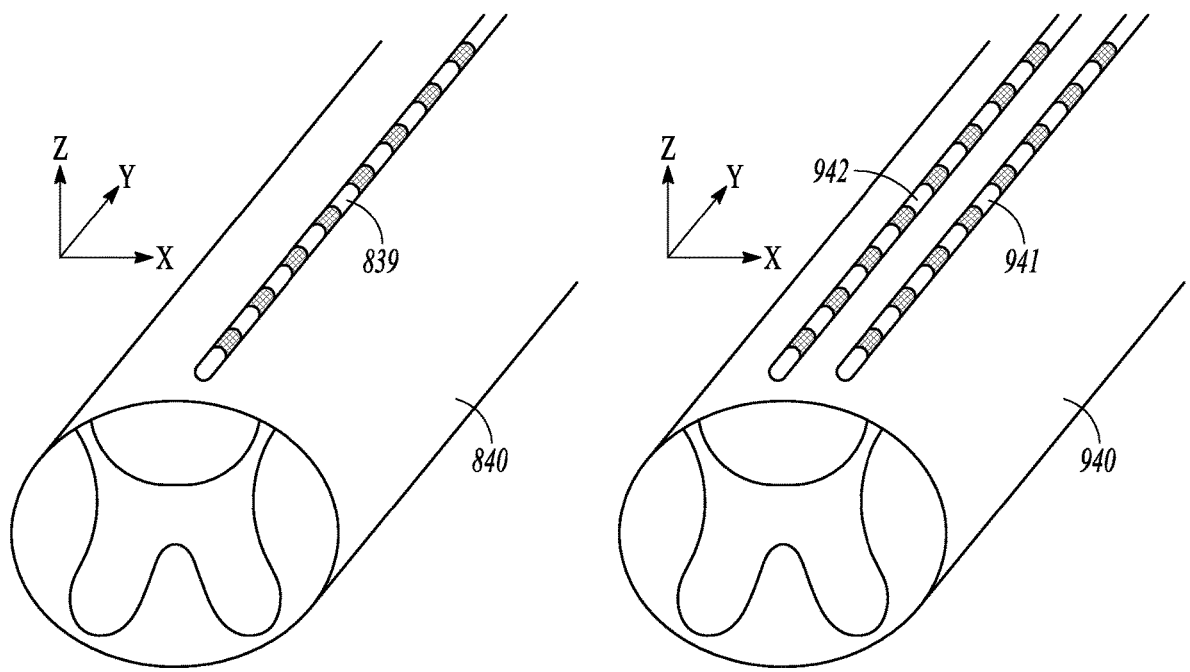
*FIG. 8*  *FIG. 9*

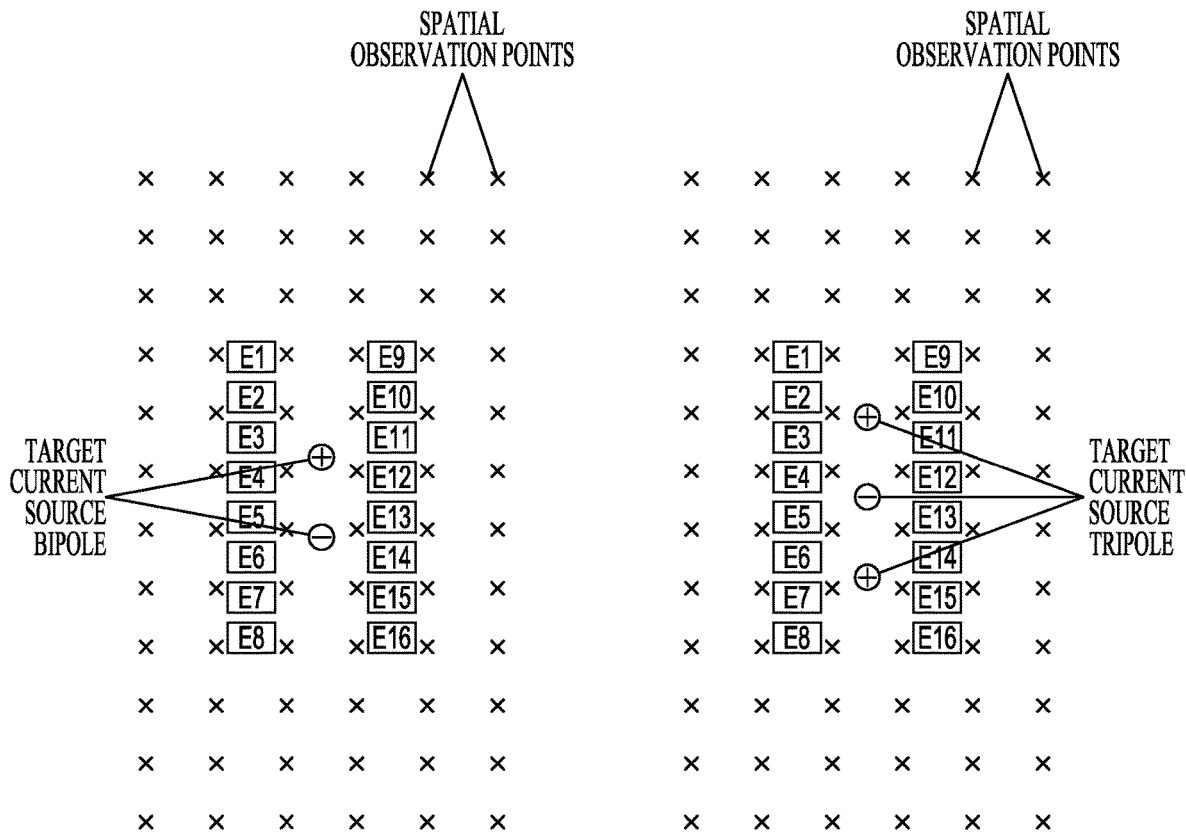
*FIG. 24A*  *FIG. 24B*
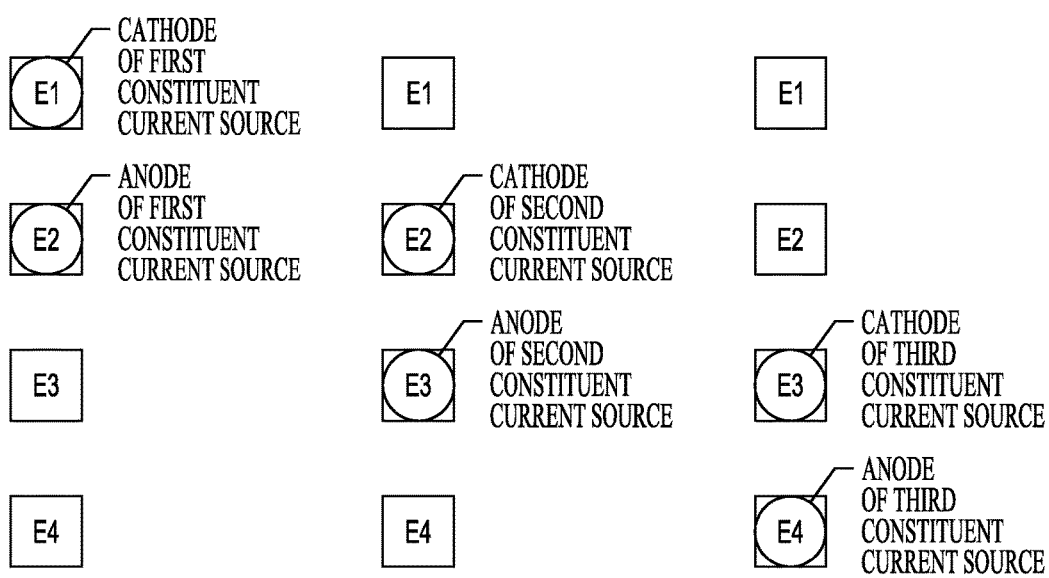
*FIG. 25A*  *FIG. 25B*  *FIG. 25C*

TRANSFER MATRIX A $(m \times n)$ $$\begin{bmatrix} m \text{ field potential values due to constituent source \#1} & m \text{ field potential values due to constituent source \#2} & m \text{ field potential values due to constituent source \#3} & \cdots & m \text{ field potential values due to constituent source \#n} \end{bmatrix}$$

*FIG. 26*

NEUROMODULATION CALIBRATION BASED ON NEUROPHYSIOLOGICAL SIGNALS

CLAIM OF PRIORITY

The application claims the benefit of priority under 35 U.S.C. § 119(e) of U.S. Provisional Patent Application Ser. No. 62/691,962, filed on Jun. 29, 2018, which is herein incorporated by reference in its entirety.

TECHNICAL FIELD

The present disclosure relates generally to medical devices, and more particularly, to neuromodulation systems, devices, and methods.

BACKGROUND

Neural modulation has been proposed as a therapy for a number of conditions. Often, neural modulation and neural stimulation may be used interchangeably to describe excitatory stimulation that causes action potentials as well as inhibitory and other effects. Examples of neuromodulation include Spinal Cord Stimulation (SCS), Deep Brain Stimulation (DBS), Peripheral Nerve Stimulation (PNS), and Functional Electrical Stimulation (FES). SCS, by way of example and not limitation, has been used to treat chronic pain syndromes. Some neural targets may be complex structures with different types of nerve fibers within a complex three dimensional environment.

SUMMARY

This Summary includes examples that provide an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

An example (e.g. Example 1) of subject matter (e.g. a system) may be configured for use with a neuromodulation device connected to at least one neuromodulation lead. The neuromodulation device may be configured to deliver neuromodulation energy to spinal cord tissue in a patient using the at least one neuromodulation lead. The subject matter may include at least one sensor configured to bilaterally sense neurophysiological signals from the patient to provide bilateral sensing data, at least one processor configured to calibrate at least a first electrode contact and a second electrode contact on the least one neuromodulation lead, including: instruct the neuromodulation device to deliver neuromodulation energy using at least the first electrode contact to cause a first neurophysiological response and using at least the second electrode contact of the lead to cause a second neurophysiological response; receive from the at least one sensor first bilateral sensed data corresponding to the first neurophysiological response and second bilateral sensed data corresponding to the second neurophysiological response; and determine based on the first and second neurophysiological responses at least one of: physiological midline information indicative of a medial-lateral position of the at least first electrode contact to the physiological midline and the at least second electrode contact to the physiological midline; or electrode-tissue coupling information indicative of a distance between the at least first electrode contact to the spinal cord tissue and a distance between the at least second electrode contact to the spinal cord tissue.

In Example 2, the subject matter of Example 1 may optionally be configured such that the at least one processor is further configured to program the neuromodulation device using at least one of the physiological midline information or the electrode-tissue coupling information.

In Example 3, the subject matter of any one or any combination of Examples 1-2 may optionally be configured such that the at least one processor is further configured to communicate the physiological midline information to a user interface to display a position of the at least one lead along with a representation of the physiological midline.

In Example 4, the subject matter of any one or any combination of Examples 1-3 may optionally be configured such that the at least one processor is further configured to communicate the physiological midline information and the electrode-tissue coupling information to a programming algorithm that is configured use the physiological midline information and the electrode-tissue coupling information to determine fractionalized energy contribution of active electrodes on the at least one lead to create a stimulation field for a three-dimensional environment. The determined fractionalized energy contribution may include a polarity for each of the active electrodes and a percentage of the energy contribution at the polarity for each of the active electrodes.

In Example 5, the subject matter of any one or any combination of Examples 1-4 may optionally be configured such that the at least one sensor includes at least one sensor configured to bilaterally sense electromyograms (EMGs) to provide bilateral sensing data.

In Example 6, the subject matter of any one or any combination of Examples 1-5 may optionally be configured such that the at least one sensor includes a plurality of EMG patches bilaterally positioned on the patient.

In Example 7, the subject matter of any one or any combination of Examples 1-6 may optionally be configured such that the at least one sensor includes: at least one sensor configured to bilaterally sense evoked compound action potentials (ECAPs) from the patient when the neural modulation energy is being delivered to provide bilateral sensing data; or at least one sensor configured to bilaterally sense electroencephalograms (EEGs) from the patient when the neural modulation energy is being delivered to provide bilateral sensing data.

In Example 8, the subject matter of any one or any combination of Examples 1-4 may optionally be configured such that the at least one sensor includes at least one sensor configured to bilaterally sense physiological signals indicative of changes in muscle tissue when the neural modulation energy is being delivered to provide bilateral sensing data.

In Example 9, the subject matter of any one or any combination of Examples 1-8 may optionally be configured such that the delivered neuromodulation energy includes monopolar neuromodulation energy.

In Example 10, the subject matter of any one or any combination of Examples 1-9 may optionally be configured such that the at least one processor is configured to calibrate a plurality of electrode contacts on the neuromodulation lead where the plurality of electrode contacts include the first and second electrode contacts. The at least one processor may be configured to determine physiological midline information and electrode-tissue coupling information for each of the plurality of electrode contacts by instructing the neuromodulation device to step through a routine to deliver neuromodulation energy to cause a plurality of neurophysiological responses such that each of the plurality of electrode contacts is associated with at least one of the neurophysiological responses.

In Example 11, the subject matter of any one or any combination of Examples 1-9 may optionally be configured such that the at least one processor is configured to calibrate less than all of a plurality of electrode contacts on the neuromodulation lead by determining physiological midline information and electrode-tissue coupling information for a first subset of the plurality of electrode contacts by instructing the neuromodulation device to step through a routine to deliver neuromodulation energy to cause a plurality of neurophysiological responses, each of the first subset of the plurality of electrode contacts being associated with at least one of the plurality of neurophysiological responses, and each of a second subset of the plurality of electrode contacts being not associated with at least one of the neurophysiological responses. The at least one processor may be configured to estimate at least one of the physiological midline information or the electrode-tissue coupling information for the second subset of the plurality of electrode contacts based on the determined physiological midline information and the electrode-tissue coupling information for the first subset of the plurality of electrode contacts.

In Example 12, the subject matter of any one or any combination of Examples 1-11 may optionally be configured such that the at least one processor is configured to calibrate the at least a first electrode contact and the second electrode contact on the least one neuromodulation lead by instructing the neuromodulation device to deliver neuromodulation energy using at least a first neuromodulation parameter set and a second neuromodulation parameter set; a neuromodulation parameter has a first value in the first neuromodulation parameter set and a second value in the second neuromodulation parameters set; and the at least on processor is configured to determine physiological midline information and electrode-tissue coupling information for the at least the first and second neuromodulation parameter sets.

In Example 13, the subject matter of Example 12 may optionally be configured such that the at least one neuromodulation parameter includes pulse width such that the first and second neuromodulation parameter sets have different pulse widths.

In Example 14, the subject matter of Example 12 may optionally be configured such that the at least one processor is configured to interpolate at least one of the physiological midline information or the electrode-tissue coupling information for a neuromodulation parameter value based on at least the first value and the second value.

An example (e.g. Example 15) of subject matter (e.g. a method, a means for performing acts, or a machine-readable medium including instructions that, when performed by the machine, cause the machine to perform acts), may calibrate at least a first electrode contact and a second electrode contact on at least one neuromodulation lead, including: instruct a neuromodulation device to deliver neuromodulation energy using at least the first electrode contact to cause a first neurophysiological response and using at least the second electrode contact of the lead to cause a second neurophysiological response; receive from at least one sensor first sensed data corresponding to the first neurophysiological response and second sensed data corresponding to the sensed neurophysiological response; determine first neurophysiological response data based on the received first sensed data and determine second neurophysiological response data based on the received second sensed data; and determine based on the first and second neurophysiological response data physiological midline information indicative of a medial-lateral position of the at least first electrode contact to the physiological midline and the at least second electrode contact to the physiological midline.

An example (e.g. Example 16) of subject matter (e.g. a method, a means for performing acts, or a machine-readable medium including instructions that, when performed by the machine, cause the machine to perform acts), may be performed using a neuromodulation device connected to at least one neuromodulation lead and configured to deliver neuromodulation energy to spinal cord tissue in a patient using the at least one neuromodulation lead, at least one processor, and at least one sensor configured to bilaterally sense neurophysiological signals from a patient to provide bilateral sensing data. The subject matter may include calibrating at least a first electrode contact and a second electrode contact on the least one neuromodulation lead, including using the at least one processor to: instruct the neuromodulation device to deliver neuromodulation energy using at least the first electrode contact to cause a first neurophysiological response and using at least the second electrode contact of the lead to cause a second neurophysiological response; receive from the at least one sensor first bilateral sensed data corresponding to the first neurophysiological response and second bilateral sensed data corresponding to the sensed neurophysiological response; determine first neurophysiological response data based on the received first bilateral sensed data and determine second neurophysiological response data based on the received second bilateral sensed data; and determine based on the first and second neurophysiological response data both: physiological midline information indicative of a medial-lateral position of the at least first electrode contact to the physiological midline and the at least second electrode contact to the physiological midline; and electrode-tissue coupling information indicative of a distance between the at least first electrode contact to the spinal cord tissue and a distance between the at least second electrode contact to the spinal cord tissue.

In Example 17, the subject matter of Example 16 may optionally be configured such that the at least one sensor includes at least one sensor configured to bilaterally sense electromyograms (EMGs).

In Example 18, the subject matter of Example 17 may optionally be configured such that the at least one sensor includes a plurality of EMG patches bilaterally positioned on the patient.

In Example 19, the subject matter of any one or any combination of Examples 16-18 may optionally be configured such that the at least one sensor includes at least one sensor configured to bilaterally sense evoked compound action potentials (ECAPs).

In Example 20, the subject matter of Example 19 may optionally be configured such that the at least one sensor includes an electrode contact on the neurostimulation lead other than an electrode contact being used to concurrently deliver neural modulation energy.

In Example 21, the subject matter of any one or any combination of Examples 16-20 may optionally be configured such that the at least one sensor includes at least one sensor configured to bilaterally sense electroencephalograms (EEGs).

In Example 22, the subject matter of Example 16 may optionally be configured such that the at least one sensor includes at least one sensor configured to bilaterally sense physiological signals indicative of changes in muscle tissue when the neural modulation energy is being delivered to provide bilateral sensing data.

In Example 23, the subject matter of any one or any combination of Examples 16-22 may optionally be configured such that the at least one processor is used to program the neuromodulator device using the physiological midline information and the electrode-tissue coupling information.

In Example 24, the subject matter of any one or any combination of Examples 16-23 may optionally be configured such that at least one processor is used to communicate the physiological midline information to a user interface to display a position of the at least one lead along with a representation of the physiological midline.

In Example 25, the subject matter of any one or any combination of Examples 16-24 may optionally be configured such that the at least one processor is used to communicate the physiological midline information and the electrode-tissue coupling information to a programming algorithm that is configured use the physiological midline information and the electrode-tissue coupling information to determine fractionalized energy contribution of active electrodes on the at least one lead to create a stimulation field for a three-dimensional environment. The determined fractionalized energy contribution may include a polarity for each of the active electrodes and a percentage of the energy contribution at the polarity for each of the active electrodes.

In Example 26, the subject matter of any one or any combination of Examples 16-25 may optionally be configured such that calibrating at least the first electrode contact and the second electrode contact on the least one neuromodulation lead includes calibrating a plurality of electrode contacts on the neuromodulation lead. The at least one processor may be used to determine physiological midline information and electrode-tissue coupling information for each of the plurality of electrode contacts by instructing the neuromodulation device to step through a routine to deliver neuromodulation energy to cause a plurality of neurophysiological responses such that each of the plurality of electrode contacts is associated with at least one of the neurophysiological responses.

In Example 27, the subject matter of any one or any combination of Examples 16-25 may optionally be configured such that calibrating at least the first electrode contact and the second electrode contact on the at least one neuromodulation lead may include calibrating less than all of a plurality of contacts on the at least one neuromodulation lead. The at least one processor may be used to determine physiological midline information and electrode-tissue coupling information for a first subset of the plurality of electrode contacts by instructing the neuromodulation device to step through a routine to deliver neuromodulation energy to cause a plurality of neurophysiological responses. Each of the first subset of the plurality of electrode contacts may be associated with at least one of the plurality of neurophysiological responses, and each of a second subset of the plurality of electrode contacts being not associated with at least one of the neurophysiological responses. The at least one processor may be used to estimate at least one of the physiological midline information or the electrode-tissue coupling information for the second subset of the plurality of electrode contacts based on the determined physiological midline information and the electrode-tissue coupling information for the first subset of the plurality of electrode contacts.

Example 28, the subject matter of any one or any combination of Examples 16-27 may optionally be configured such that calibrating the at least a first electrode contact and the second electrode contact on the least one neuromodulation lead includes instructing the neuromodulation device to deliver neuromodulation energy using at least a first neuromodulation parameter set and a second neuromodulation parameter set; a neuromodulation parameter has a first value in the first neuromodulation parameter set and a second value in the second neuromodulation parameters set; and using the at least one processor to determine physiological midline information and electrode-tissue coupling information for the at least the first and second neuromodulation parameter sets.

In Example 29, the subject matter of Example 28 may optionally be configured such that the at least one processor is used to interpolate at least one of the physiological midline information or the electrode-tissue coupling information for a neuromodulation parameter value based on at least the first value and the second value.

An example (e.g. Example 30) of subject matter (e.g. a system) may be configured for use with a neuromodulation device connected to at least one neuromodulation lead where the neuromodulation device is configured to deliver neuromodulation energy to spinal cord tissue in a patient using the at least one neuromodulation lead. The system may include at least one sensor configured to sense neurophysiological signals from the patient to provide sensing data; and at least one processor configured to calibrate at least a first electrode contact and a second electrode contact on the least one neuromodulation lead, including: instruct the neuromodulation device to deliver neuromodulation energy using at least the first electrode contact to cause a first neurophysiological response and using at least the second electrode contact of the lead to cause a second neurophysiological response; receive from the at least one sensor first sensed data corresponding to the first neurophysiological response and second sensed data corresponding to the second neurophysiological response; and determine based on the first and second neurophysiological responses physiological midline information indicative of a medial-lateral position of the at least first electrode contact to the physiological midline and the at least second electrode contact to the physiological midline.

In Example 31, the subject matter of Example 30 may optionally be configured such that the at least one sensor may be configured to bilaterally sense neurophysiological signals from the patient to provide bilateral sensing data. By way of example and not limitation, the at least one sensor may include at least one sensor laterally positioned on the left side the midline and at least one sensor laterally positioned on the right side of the midline to bilaterally sense neurophysiological signals from the patient to provide bilateral sensing data.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 7 illustrates, by way of example, some features of the neuromodulation leads and a waveform generator.

FIG. 8 is a schematic view of an example of a single electrical modulation lead implanted over approximately the longitudinal midline of the patient's spinal cord.

FIG. 9 is a schematic view of an example of two electrical modulation leads.

FIGS. 24A-24B illustrate, by way of example, mapping a target electrical field to an electrode array.

FIGS. 25A-25C, illustrate, by way of example, selection of a plurality of constituent current sources at the locations of the electrodes.

FIG. 26 illustrates an m×n transfer matrix used to determine the relative strengths of constituent current sources.

DETAILED DESCRIPTION

Figure 1:
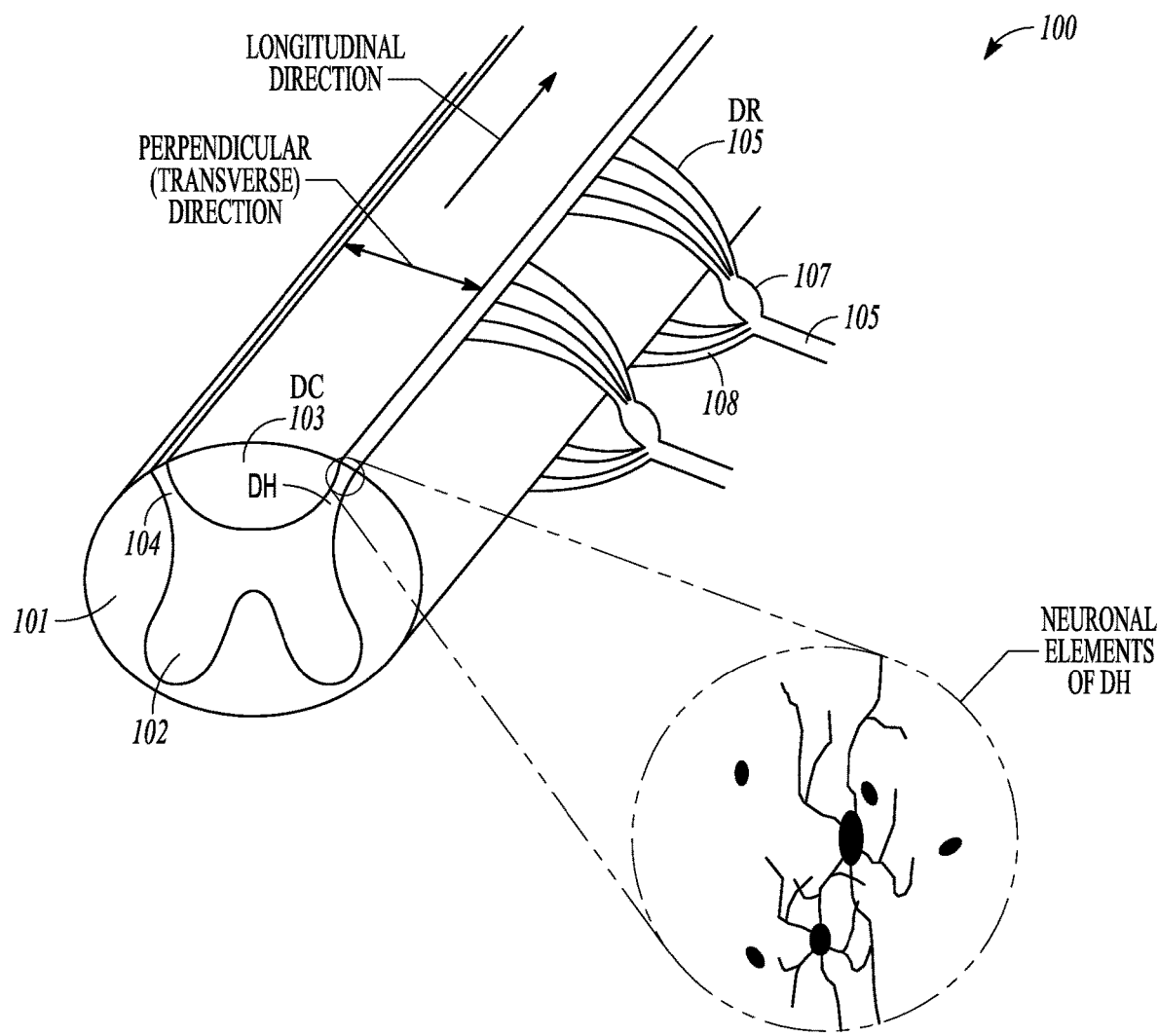
FIG. 1 illustrates, by way of example and not limitation, a portion of a spinal cord including white matter and gray matter of the spinal cord.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Various embodiments described herein involve spinal cord modulation. The complex spinal cord structure resides in a complex three-dimensional environment. For example, the thickness of the cerebrospinal fluid (CSF), which is between the spinal cord and the epidural space, varies along the spine. Thus, the distance between the spinal cord and one or more neuromodulation leads within the epidural space likely varies. Furthermore, neither the leads nor the spinal cord form simple straight lines. The positions of implanted neuromodulation leads can also vary and are not perfectly parallel to the spinal cord. Additionally, the neuroanatomy of the spinal cord region can vary from patient-to-patient. It is desirable to accurately calibrate a modulation system to account for electrode positions and variations in conductance through the electrodes and tissue to improve therapy programming. Patient perception thresholds may be used to calibrate the electric field generated using the electrodes. However, significant limitations with using patient perception include that it is subjective, it is time consuming requiring multiple amplitude adjustments until the patient perception threshold is obtained, it fails to provide medio-lateral calibration, and it fails to account for midline drifts within the spinal cord. As perception may change with different modulation parameters (e.g. pulse width), the time consuming, subjective routine is repeated to calibrate the electrodes for different pulse widths.

Various embodiments of the present subject matter provide an objective calibration of the electrodes both rostrocaudally and mediolaterally that enables accurate programming of the neuromodulation device. The objective calibration implemented by the present subject matter is faster than the subjective calibration that finds patient perception thresholds. The automated rostrocaudal and mediolateral calibration of the electrode contacts improves programming of field shapes towards the dorsal horn and can guide programming by illustrating a representation of the physiological midline. Furthermore, the automated calibration may be performed for a plurality of pulse widths and frequencies to account for variations attributable to pulse width for frequency differences. Also, as the calibration is objectively performed using sensors, the calibration may be performed with the patient sedated (e.g. asleep), which may be desirable for both the patient and clinician.

A brief description of the physiology of the spinal cord is provided herein to assist the reader. FIG. 1 illustrates, by way of example, a portion of a spinal cord 100 including white matter 101 and gray matter 102 of the spinal cord. The gray matter 102 includes cell bodies, synapse, dendrites, and axon terminals. White matter 101 includes myelinated axons that connect gray matter areas. A typical transverse section of the spinal cord includes a central "butterfly" shaped central area of gray matter 102 substantially surrounded by an ellipse-shaped outer area of white matter 101. The white matter of the dorsal column (DC) 103 includes mostly large myelinated axons that form afferent fibers that run in an axial direction. The dorsal portions of the "butterfly" shaped central area of gray matter are referred to as dorsal horns (DH) 104. In contrast to the DC fibers that run in an axial direction, DH fibers can be oriented in many directions, including perpendicular to the longitudinal axis of the spinal cord. Examples of spinal nerves 105 are also illustrated, including a dorsal root (DR) 105, dorsal root ganglion 107 and ventral root 108. The dorsal root 105 mostly carries sensory signals into the spinal cord, and the ventral root functions as an efferent motor root. The dorsal and ventral roots join to form mixed spinal nerves 105.

SCS has been used to alleviate pain. A therapeutic goal for conventional SCS programming has been to maximize stimulation (i.e., recruitment) of the DC fibers that run in the white matter along the longitudinal axis of the spinal cord and minimal stimulation of other fibers that run perpendicular to the longitudinal axis of the spinal cord (dorsal root fibers, predominantly), as illustrated in FIG. 1. The white matter of the DC includes mostly large myelinated axons that form afferent fibers. While the full mechanisms of pain relief are not well understood, it is believed that the perception of pain signals is inhibited via the gate control theory of pain, which suggests that enhanced activity of innocuous touch or pressure afferents via electrical stimulation creates interneuronal activity within the DH of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been conventionally targeted for stimulation at an amplitude that provides pain relief. Current implantable neuromodulation systems typically include electrodes implanted adjacent, i.e., resting near, or upon the dura, to the dorsal column of the spinal cord of the patient and along a longitudinal axis of the spinal cord of the patient.

Activation of large sensory DC nerve fibers also typically creates the paresthesia sensation that often accompanies conventional SCS therapy. Although alternative or artifactual sensations, such as paresthesia, are usually tolerated relative to the sensation of pain, patients sometimes report these sensations to be uncomfortable, and therefore, they can be considered an adverse side-effect to neuromodulation therapy in some cases. Some embodiments deliver sub-perception therapy that is therapeutically effective to treat pain, for example. However, the patient does not sense the delivery of the modulation field (e.g. paresthesia) during a sub-perception therapy. Sub-perception therapy may modulate the spinal cord using a relatively high frequency modulation (e.g. about 1000 Hz or above). The high frequency modulation may include 1200 Hz or above, and may include 1500 Hz or above. Some embodiments herein selectively modulate DH tissue over DC tissue. Some embodiments selectively stimulate DR tissue and/or dorsal root ganglion over DC tissue to provide sub-perception therapy. As will be described in further detail below, some embodiments described herein target axons from inhibitory interneurons that propagate in anterior-posterior direction aligned with an electric field. Certain myelinated presynaptic terminals of inhibitory neurons oriented in the anterior-posterior (AP) direction, i.e. in parallel with electric field, may polarize more than their unmyelinated, differently oriented counterparts. Polarization may produce both subthreshold and suprathreshold effects that result in positive clinical effects.

Such selective modulation may be delivered at frequencies less than 1,200 Hz. The selective modulation may be delivered at frequencies less than 1,000 Hz in some embodiments. In some embodiments, the selective modulation may be delivered at frequencies less than 500 Hz. In some embodiments, the selective modulation may be delivered at frequencies less than 350 Hz. In some embodiments, the selective modulation may be delivered at frequencies less than 130 Hz. The selective modulation may be delivered at low frequencies (e.g. as low as 2 Hz). The selective modulation may be delivered even without pulses (e.g. 0 Hz) to modulate some neural tissue. By way of example and not limitation, it is further noted that the selective modulation may be delivered with a duty cycle, in which stimulation (e.g. a train of pulses) is delivered during a Stimulation ON portion of the duty cycle, and is not delivered during a Stimulation OFF portion of the duty cycle. The selected modulation may be delivered with fixed or variable pulse widths.

Figure 2:
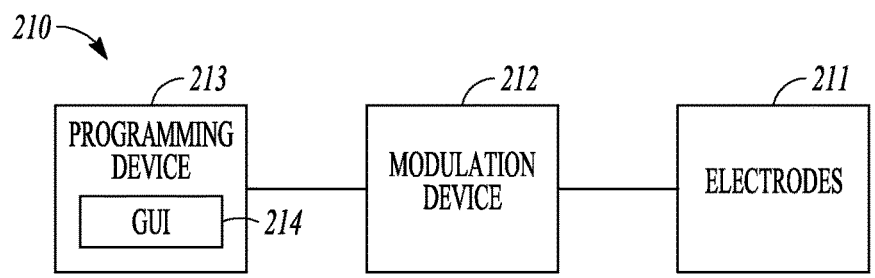
FIG. 2 illustrates, by way of example, an embodiment of a neuromodulation system.

FIG. 2 illustrates, by way of example, an embodiment of a neuromodulation system. The illustrated system 210 includes electrodes 211, a modulation device 212, and a programming system such as a programming device 213. The programming system may include multiple devices. The electrodes 211 are configured to be placed on or near one or more neural targets in a patient. For example, the electrodes 211 may be on one or more leads implanted within the subdural space of the spinal cord. The modulation device 212 is configured to be electrically connected to electrodes 211 and deliver modulation energy, such as in the form of electrical pulses, to the one or more neural targets though electrodes 211. The delivery of the modulation energy is controlled by using a plurality of modulation parameters. The modulation parameters may specify the electrical waveform (e.g. pulses or pulse patterns or other waveform shapes) and a selection of electrodes through which the electrical waveform is delivered. In various embodiments, at least some parameters of the plurality of modulation parameters are programmable by a user, such as a physician or other caregiver. The programming device 213 provides the user with accessibility to the user-programmable parameters. In various embodiments, the programming device 213 is configured to be communicatively coupled to modulation device via a wired or wireless link. In various embodiments, the programming device 213 includes a graphical user interface (GUI) 214 that allows the user to set and/or adjust values of the user-programmable modulation parameters.

Figure 3:
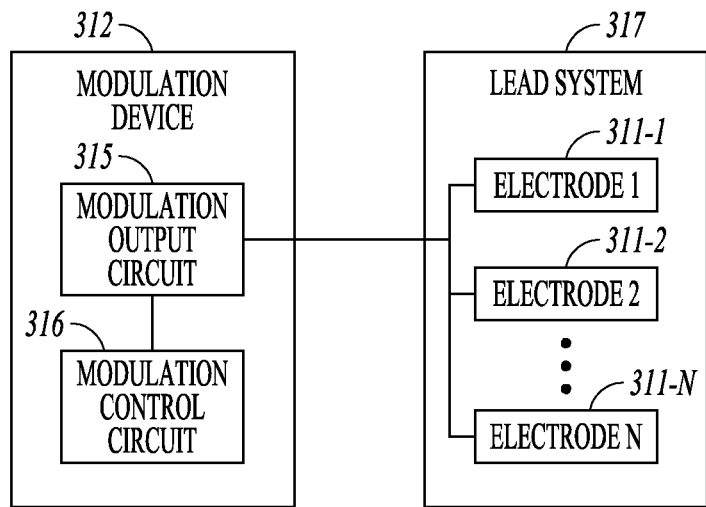
FIG. 3 illustrates an embodiment of a modulation device, such as may be implemented in the neuromodulation system of FIG. 2.

FIG. 3 illustrates an embodiment of a modulation device 312, such as may be implemented in the neuromodulation system 210 of FIG. 2. The illustrated embodiment of the modulation device 312 includes a modulation output circuit 315 and a modulation control circuit 316. Those of ordinary skill in the art will understand that the neuromodulation system 210 may include additional components such as sensing circuitry for patient monitoring and/or feedback control of the therapy, telemetry circuitry and power. The modulation output circuit 315 produces and delivers the modulation energy. Neuromodulation pulses are provided herein as an example. However, the present subject matter is not limited to pulses, but may include other electrical waveforms (e.g. waveforms with different waveform shapes, and waveforms with various pulse patterns). The modulation control circuit 316 controls the delivery of the neuromodulation pulses or other waveforms using the plurality of neuromodulation parameters. The lead system 317 includes one or more leads each configured to be electrically connected to modulation device 312 and a plurality of electrodes 311-1 to 311-N distributed in an electrode arrangement using the one or more leads. Each lead may have an electrode array consisting of two or more electrodes, which also may be referred to as contacts. Multiple leads may provide multiple electrode arrays to provide the electrode arrangement. Each electrode is a single electrically conductive contact providing for an electrical interface between modulation output circuit 315 and tissue of the patient, where N≥2. The neuromodulation pulses are each delivered from the modulation output circuit 315 through a set of electrodes selected from the electrodes 311-1 to 311-N. The number of leads and the number of electrodes on each lead may depend on, for example, the distribution of target(s) of the neuromodulation and the need for controlling the distribution of electric field at each target. In one embodiment, by way of example and not limitation, the lead system includes two leads each having eight electrodes. Some embodiments may use a lead system that includes a paddle lead.

The neuromodulation system may be configured to modulate spinal target tissue or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. An electrical waveform may be controlled or varied for delivery using electrode configuration(s). The electrical waveforms may be analog or digital signals. In some embodiments, the electrical waveform includes pulses. The pulses may be delivered in a regular, repeating pattern, or may be delivered using complex patterns of pulses that appear to be irregular. Other parameters that may be controlled or varied include the amplitude, pulse width, and rate (or frequency) of the electrical pulses. Each electrode configuration, along with the electrical pulse parameters, can be referred to as a "modulation parameter set." Each set of modulation parameters, including fractionalized current distribution to the electrodes (as percentage cathodic current, percentage anodic current, or off), may be stored and combined into a modulation program that can then be used to modulate multiple regions within the patient.

The number of electrodes available combined with the ability to generate a variety of complex electrical waveforms (e.g. pulses) presents a huge selection of modulation parameter sets to the clinician or patient. For example, if the neuromodulation system to be programmed has sixteen electrodes, millions of modulation parameter sets may be available for programming into the neuromodulation system. Furthermore, for example, SCS systems may have thirty-two electrodes which exponentially increases the number of modulation parameters sets available for programming. To facilitate such selection, the clinician generally programs the modulation parameter sets through a computerized programming system to allow the optimum modulation parameters to be determined based on patient feedback or other means and to subsequently program the desired modulation parameter sets.

Figure 4:
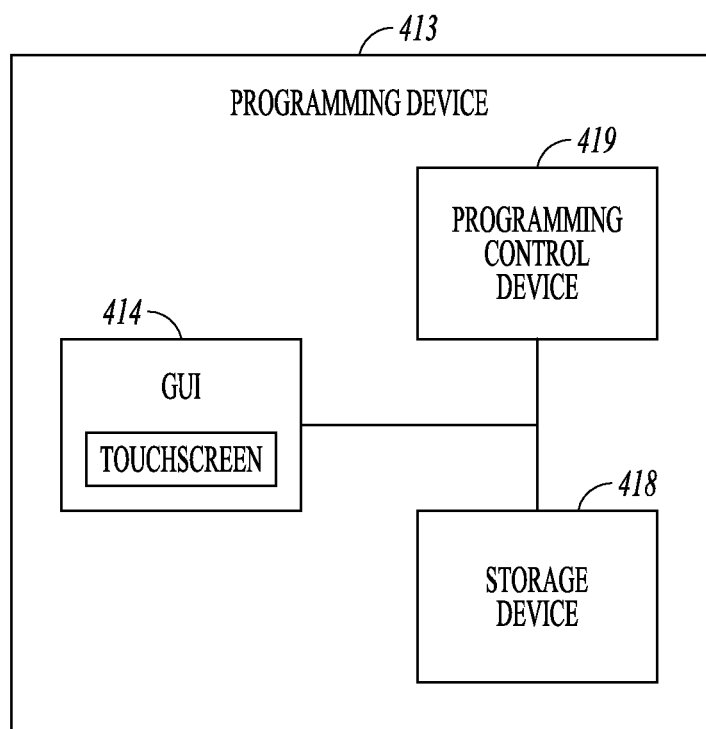
FIG. 4 illustrates an embodiment of a programming system such as a programming device, which may be implemented as the programming device in the neuromodulation system of FIG. 2.

FIG. 4 illustrates an embodiment of a programming system such as a programming device 413, which may be implemented as the programming device 213 in the neuromodulation system of FIG. 2. The programming device 413 includes a storage device 418, a programming control circuit 419, and a GUI 414. The programming control circuit 419 generates the plurality of modulation parameters that controls the delivery of the neuromodulation pulses according to the pattern of the neuromodulation pulses. In various embodiments, the GUI 414 includes any type of presentation device, such as interactive or non-interactive screens, and any type of user input devices that allow the user to program the modulation parameters, such as touchscreen, keyboard, keypad, touchpad, trackball, joystick, and mouse. The storage device 418 may store, among other things, modulation parameters to be programmed into the modulation device. The programming device 413 may transmit the plurality of modulation parameters to the modulation device. In some embodiments, the programming device 413 may transmit power to the modulation device. The programming control circuit 419 may generate the plurality of modulation parameters. In various embodiments, the programming control circuit 419 may check values of the plurality of modulation parameters against safety rules to limit these values within constraints of the safety rules.

In various embodiments, circuits of neuromodulation, including various embodiments discussed in this document, may be implemented using a combination of hardware, software and firmware. For example, the circuit of GUI, modulation control circuit, and programming control circuit, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 5:
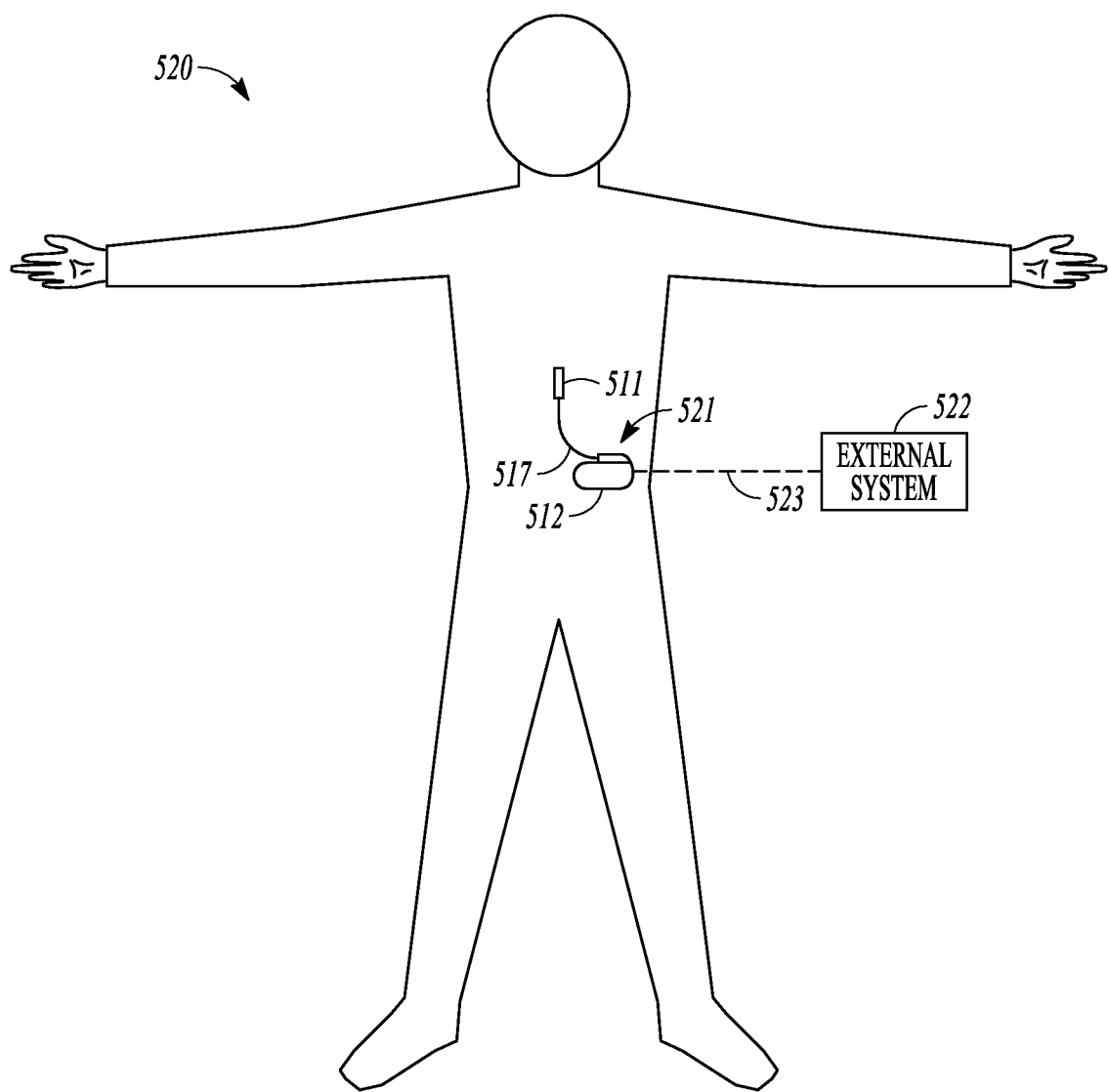
FIG. 5 illustrates, by way of example, an implantable neuromodulation system and portions of an environment in which system may be used.

FIG. 5 illustrates, by way of example, an implantable neuromodulation system and portions of an environment in which system may be used. The system is illustrated for implantation near the spinal cord. The illustrated system 520 includes an implantable system 521, an external system 522, and a telemetry link 523 providing for wireless communication between implantable system 521 and external system 522. The system 520 is illustrated as being implanted in the patient's body. The implantable system 521 includes an implantable neuromodulation device (also referred to as an implantable pulse generator, or IPG) 512, a lead system 517, and electrodes 511. The lead system 517 includes one or more leads each configured to be electrically connected to the modulation device 512 and a plurality of electrodes 511 distributed in the one or more leads. In various embodiments, the external system 522 includes one or more external (non-implantable) devices each allowing a user (e.g. a clinician or other caregiver and/or the patient) to communicate with the implantable system 521. In some embodiments, the external system 522 includes a programming device intended for a clinician or other caregiver to initialize and adjust settings for the implantable system 521 and a remote control device intended for use by the patient. For example, the remote control device may allow the patient to turn a therapy on and off and/or adjust certain patient-programmable parameters of the plurality of modulation parameters.

The neuromodulation lead(s) of the lead system 517 may be placed adjacent, i.e., resting near, or upon the dura, adjacent to the spinal cord area to be stimulated. For example, the neuromodulation lead(s) may be implanted along a longitudinal axis of the spinal cord of the patient. Due to the lack of space near the location where the neuromodulation lead(s) exit the spinal column, the implantable modulation device 512 may be implanted in a surgically-made pocket either in the abdomen or above the buttocks, or may be implanted in other locations of the patient's body. The lead extension(s) may be used to facilitate the implantation of the implantable modulation device 512 away from the exit point of the neuromodulation lead(s).

Figure 6:
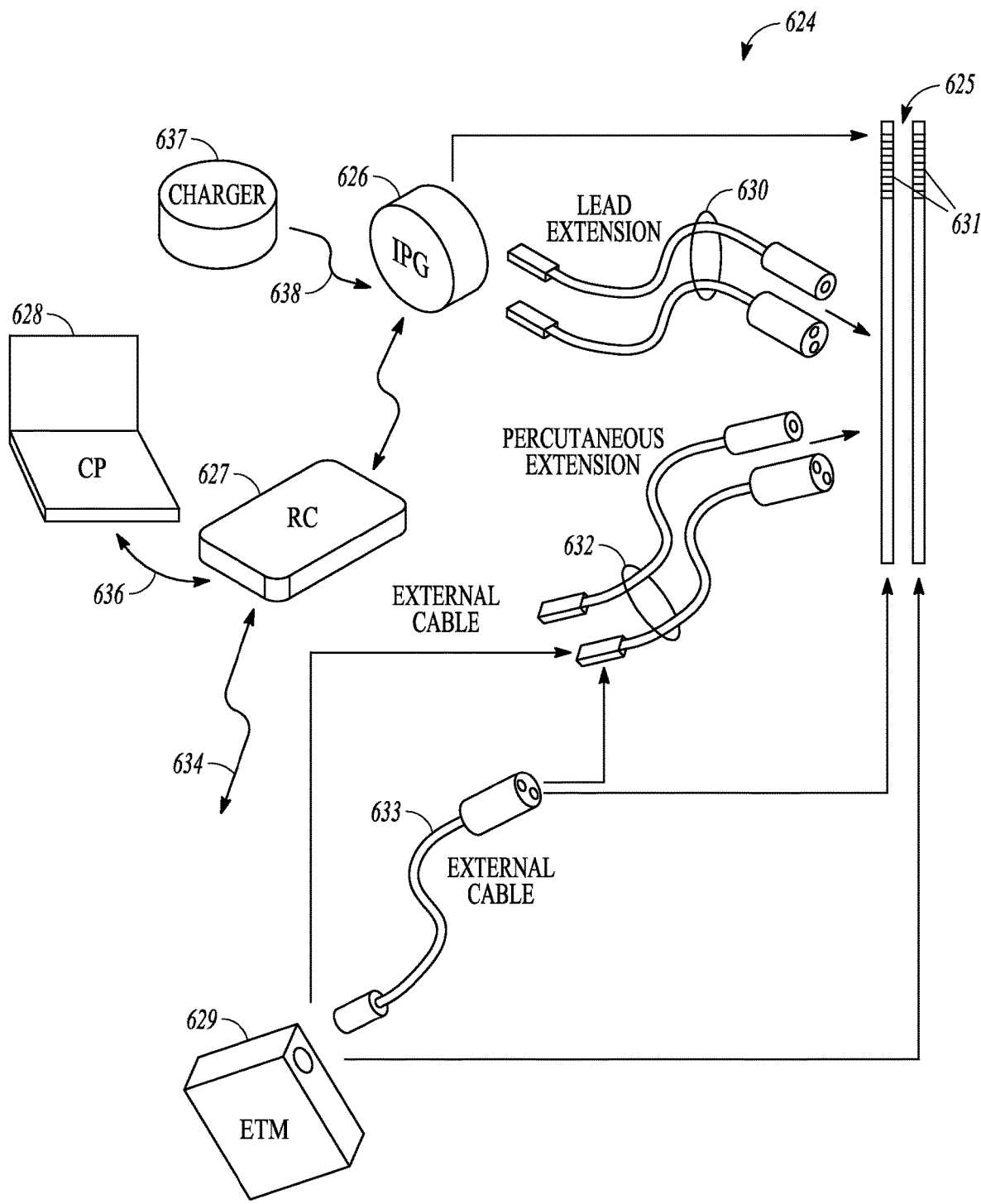
FIG. 6 illustrates, by way of example, an embodiment of a SCS system.

FIG. 6 illustrates, by way of example, an embodiment of a SCS system, which also may be referred to as a Spinal Cord Modulation (SCM) system. The SCS system 624 may generally include a plurality (illustrated as two) of implantable neuromodulation leads 625, an electrical waveform generator 626, an external remote controller RC 627, a clinician's programmer (CP) 628, and an external trial modulator (ETM) 629. IPGs are used herein as an example of the electrical waveform generator. However, it is expressly noted that the waveform generator may be configured to deliver repeating patterns of pulses, irregular patterns of pulses where pulses have differing amplitudes, pulse widths, pulse intervals, and bursts with differing number of pulses. It is also expressly noted that the waveform generator may be configured to deliver electrical waveforms other than pulses. The waveform generator 626 may be physically connected via one or more percutaneous lead extensions 630 to the neuromodulation leads 625, which carry a plurality of electrodes 631. As illustrated, the neuromodulation leads 625 may be percutaneous leads with the electrodes arranged in-line along the neuromodulation leads. Any suitable number of neuromodulation leads can be provided, including only one. A surgical paddle lead can be used in place of one or more of the percutaneous leads. In some embodiments, the waveform generator 626 may include pulse generation circuitry that delivers electrical modulation energy in the form of a pulsed electrical waveform (i.e., a temporal series of electrical pulses) to the electrodes in accordance with a set of modulation parameters.

The ETM 629 may also be physically connected via the percutaneous lead extensions 632 and external cable 633 to the neuromodulation leads 625. The ETM 629 may have similar waveform generation circuitry as the waveform generator 626 to deliver electrical modulation energy to the electrodes accordance with a set of modulation parameters. The ETM 629 is a non-implantable device that is used on a trial basis after the neuromodulation leads 625 have been implanted and prior to implantation of the waveform generator 626, to test the responsiveness of the modulation that is to be provided. Functions described herein with respect to the waveform generator 626 can likewise be performed with respect to the ETM 629.

The RC 627 may be used to telemetrically control the ETM 629 via a bi-directional RF communications link 634. The RC 627 may be used to telemetrically control the waveform generator 626 via a bi-directional RF communications link 635. Such control allows the waveform generator 626 to be turned on or off and to be programmed with different modulation parameter sets. The waveform generator 626 may also be operated to modify the programmed modulation parameters to actively control the characteristics of the electrical modulation energy output by the waveform generator 626. A clinician may use the CP 628 to program modulation parameters into the waveform generator 626 and ETM 629 in the operating room and in follow-up sessions.

The CP 628 may indirectly communicate with the waveform generator 626 or ETM 629, through the RC 627, via an IR communications link 636 or other link. The CP 628 may directly communicate with the waveform generator 626 or ETM 629 via an RF communications link or other link (not shown). The clinician detailed modulation parameters provided by the CP 628 may also be used to program the RC 627, so that the modulation parameters can be subsequently modified by operation of the RC 627 in a stand-alone mode (i.e., without the assistance of the CP 628). Various devices may function as the CP 628. Such devices may include portable devices such as a lap-top personal computer, mini-computer, personal digital assistant (PDA), tablets, phones, or a remote control (RC) with expanded functionality. Thus, the programming methodologies can be performed by executing software instructions contained within the CP 628. Alternatively, such programming methodologies can be performed using firmware or hardware. In any event, the CP 628 may actively control the characteristics of the electrical modulation generated by the waveform generator 626 to allow the desired parameters to be determined based on patient feedback or other feedback and for subsequently programming the waveform generator 626 with the desired modulation parameters. To allow the user to perform these functions, the CP 628 may include a user input device (e.g., a mouse and a keyboard), and a programming display screen housed in a case. In addition to, or in lieu of, the mouse, other directional programming devices may be used, such as a trackball, touchpad, joystick, touch screens or directional keys included as part of the keys associated with the keyboard. An external device (e.g. CP) may be programmed to provide display screen(s) that allow the clinician to, among other functions, to select or enter patient profile information (e.g., name, birth date, patient identification, physician, diagnosis, and address), enter procedure information (e.g., programming/follow-up, implant trial system, implant waveform generator, implant waveform generator and lead(s), replace waveform generator, replace waveform generator and leads, replace or revise leads, explant, etc.), generate a pain map of the patient, define the configuration and orientation of the leads, initiate and control the electrical modulation energy output by the neuromodulation leads, and select and program the IPG with modulation parameters in both a surgical setting and a clinical setting.

An external charger 637 may be a portable device used to transcutaneously charge the waveform generator via a wireless link such as an inductive link 638. Once the waveform generator has been programmed, and its power source has been charged by the external charger or otherwise replenished, the waveform generator may function as programmed without the RC or CP being present.

FIG. 7 illustrates, by way of example, some features of the neuromodulation leads 725 and a waveform generator 726. The waveform generator 726 may be an implantable device or may be an external device such as may be used to test the electrodes during an implantation procedure. In the illustrated example, one of the neuromodulation leads has eight electrodes (labeled E1-E8), and the other neuromodulation lead has eight electrodes (labeled E9-E16). The actual number and shape of leads and electrodes may vary for the intended application. An implantable waveform generator may include an outer case for housing the electronic and other components. The outer case may be composed of an electrically conductive, biocompatible material, such as titanium, that forms a hermetically-sealed compartment wherein the internal electronics are protected from the body tissue and fluids. In some cases, the outer case may serve as an electrode (e.g. case electrode). The waveform generator may include electronic components, such as a controller/processor (e.g., a microcontroller), memory, a battery, telemetry circuitry, monitoring circuitry, modulation output circuitry, and other suitable components known to those skilled in the art. The microcontroller executes a suitable program stored in memory, for directing and controlling the neuromodulation performed by the waveform generator. Electrical modulation energy is provided to the electrodes in accordance with a set of modulation parameters programmed into the pulse generator. By way of example but not limitation, the electrical modulation energy may be in the form of a pulsed electrical waveform. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (measured in milliamps or volts depending on whether the pulse generator supplies constant current or constant voltage to the electrode array), pulse width (measured in microseconds), pulse rate (measured in pulses per second), and burst rate (measured as the modulation on duration X and modulation off duration Y). Electrodes that are selected to transmit or receive electrical energy are referred to herein as "activated," while electrodes that are not selected to transmit or receive electrical energy are referred to herein as "non-activated."

Electrical modulation occurs between or among a plurality of activated electrodes, one of which may be the case of the waveform generator. The system may be capable of transmitting modulation energy to the tissue in a monopolar or multipolar (e.g., bipolar, tripolar, etc.) fashion. Monopolar modulation occurs when a selected one of the lead electrodes is activated along with the case of the waveform generator, so that modulation energy is transmitted between the selected electrode and case. Any of the electrodes E1-E16 and the case electrode may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (anode, sourcing current), negative (cathode, sinking current), or off (no current) polarity in any of the k timing channels. The waveform generator may be operated in a mode to deliver electrical modulation energy that is therapeutically effective and causes the patient to perceive delivery of the energy (e.g. therapeutically effective to relieve pain with perceived paresthesia), and may be operated in a sub-perception mode to deliver electrical modulation energy that is therapeutically effective and does not cause the patient to perceive delivery of the energy (e.g. therapeutically effective to relieve pain without perceived paresthesia).

The waveform generator may be configured to individually control the magnitude of electrical current flowing through each of the electrodes. For example, a current generator may be configured to selectively generate individual current-regulated amplitudes from independent current sources for each electrode. In some embodiments, the pulse generator may have voltage regulated outputs. While individually programmable electrode amplitudes are desirable to achieve fine control, a single output source switched across electrodes may also be used, although with less fine control in programming. Neuromodulators may be designed with mixed current and voltage regulated devices. Calibration techniques are used to determine the proper current fractionalization. With the current fractionalized to a plurality of electrodes on the electrical modulation lead, the resulting field can be calculated by superimposing the fields generated by the current delivered to each electrode. Moreover, each electrical field has a longitudinal component and a transverse component.

FIG. 8 is a schematic view of a single electrical modulation lead 839 implanted over approximately the longitudinal midline of the patient's spinal cord 840. It is understood that additional leads or lead paddle(s) may be used, such as may be used to provide a wider electrode arrangement and/or to provide the electrodes closer to dorsal horn elements, and that these electrode arrays also may implement fractionalized current. FIG. 9 illustrates an embodiment where an electrical modulation lead 941 has been implanted more laterally with respect to the spinal cord, thereby placing it proximate the dorsal horn of the spinal cord, and the other electrical modulation lead 942 has been implanted more medially with respect to the spinal cord, thereby placing it proximate the dorsal column of the spinal cord 940. Placement of the lead more proximate to the DH than the DC may be desirable to preferentially stimulate DH elements over DC neural elements for a sub-perception therapy. Any other plurality of leads or a multiple column paddle lead can also be used. A longitudinal component of the electrical field is directed along the y-axis depicted in FIG. 8, and a transverse component of the electrical field is directed along the x-axis depicted in FIG. 8. Some embodiments may include directional leads with one or more directional electrodes. A directional electrode may extend less than 360 degrees about the circumference of a lead body. For example, a row of two or more directional electrodes (e.g. "segmented electrodes") may be positioned along the circumference of the lead body. Activating select ones of the segmented electrodes may help extend and shape the field in a preferred direction.

Figure 10:
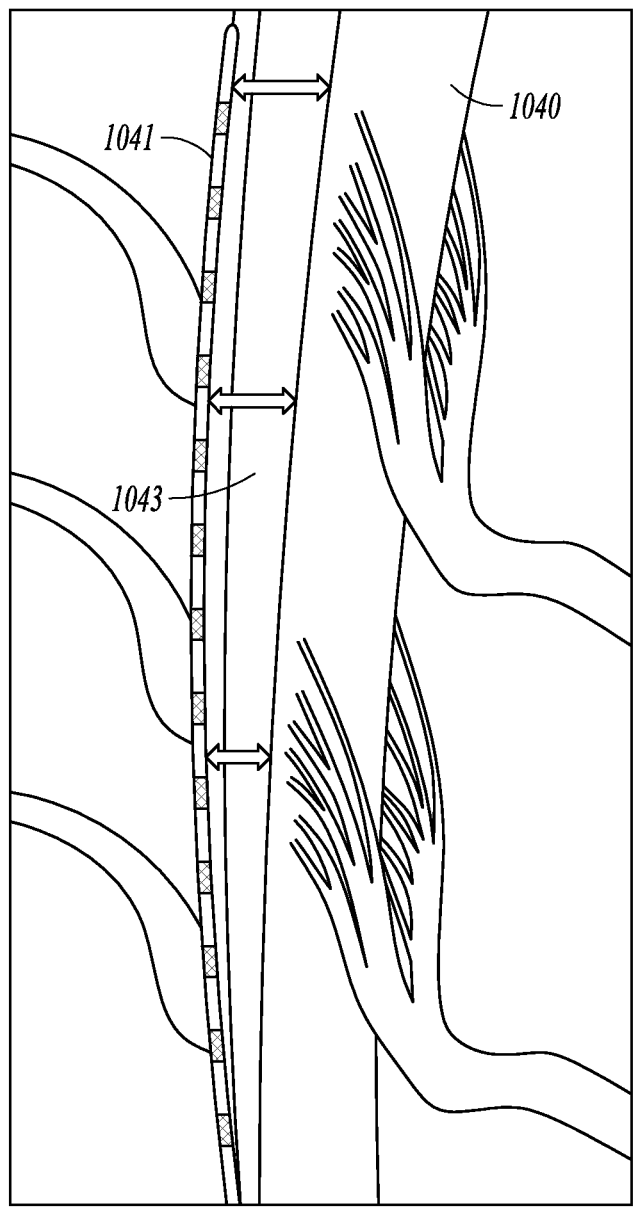
FIG. 10 illustrates, by way of example, a side view of a spinal cord and lead.
Figure 11:
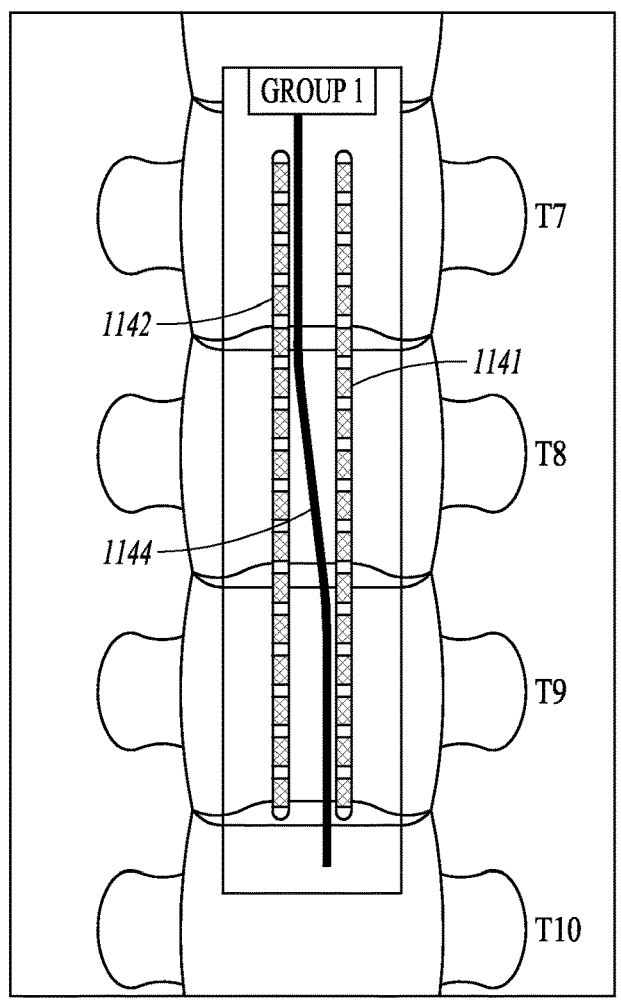
FIG. 11 illustrates, by way of example, a physiological midline for the spinal cord.
Figure 12:
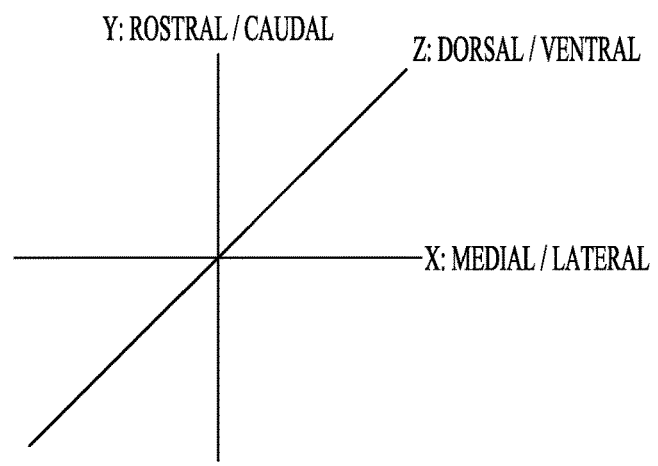
FIG. 12 illustrates a coordinate system.

FIGS. 10-12 illustrate some of the complexities of the neuroanatomical structure of the spinal cord and the complex three-dimensional environment of the leads and spinal cord. FIG. 10 illustrates a side view of a spinal cord 1040 and lead 1041, and further illustrates that neither the lead nor the spinal cord is a simple line and illustrates that the distance between the lead and the spinal cord tissue can vary. For example, the SCF 1043 may be thicker at different vertebral levels. With reference to the coordinate system illustrated in FIG. 12, variations in the distance between the spinal cord and lead generally correspond to variations in the Z axis (dorsal/ventral directions). Additionally, with reference to both FIGS. 11 and 12, the leads 1141 and 1142 and neuroanatomy of the spinal cord may have mediolateral variations, which generally correspond to variations in the X axis (medial/lateral directions). FIG. 11 illustrates a physiological midline 1144 for the spinal cord. The leads generally run in the Y axis (rostral/caudal directions).

Figure 13:
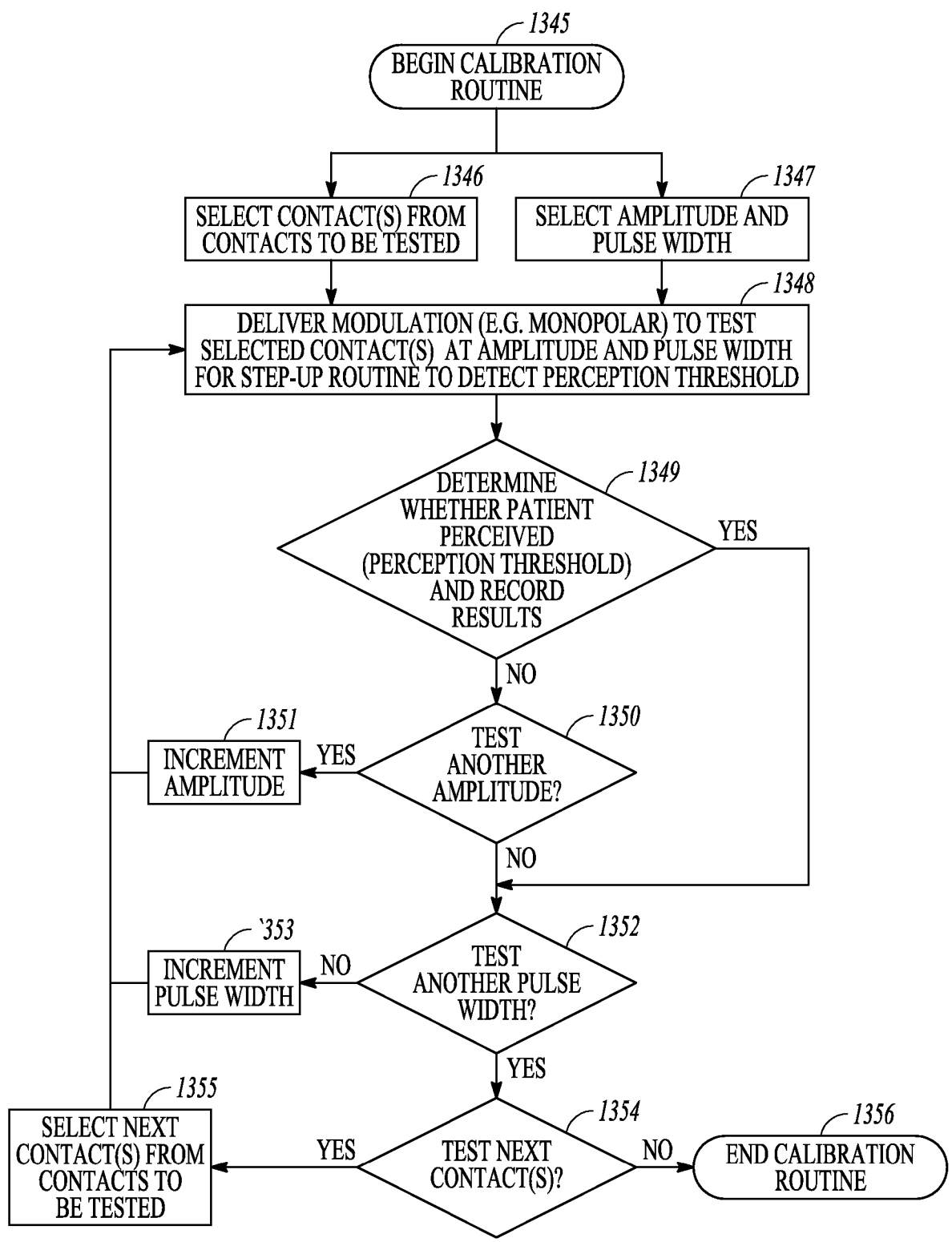
FIG. 13 illustrates a prior art, subjective method for calibrating electrodes for a neuromodulation therapy using patient perception threshold.

As identified previously, it is desirable to accurately account for electrode positions to improve therapy programming. Patient perception thresholds may be used to calibrate the electrodes, but significant limitations with using patient perception include that it is subjective, it is time consuming requiring multiple amplitude adjustments until the patient perception threshold is obtained, it fails to provide mediolateral calibration, and it fails to account for midline drifts within the spinal cord. Finally, as perception may change with different modulation parameters (e.g. pulse width), the time consuming, subjective routine is repeated to calibrate the electrodes for different pulse widths. FIG. 13 illustrates a prior art, subjective method for calibrating electrodes for a neuromodulation therapy using patient perception threshold. The illustrated routine begins at 1345. A clinician may select the electrode contact or contacts to be tested 1346, and may also select the amplitude and pulse width of a modulation signal used to deliver the modulation energy via the selected electrode contact(s) 1347. The modulation energy may be delivered as a monopolar signal, and a step-up routine may be implemented. To perform such a step-up routine, the clinician may set the amplitude significantly low to ensure that the patient cannot perceive the energy. The modulation energy is delivered at 1348, and after a period of time, the clinician may ask if the patient can perceive the energy (e.g. paresthesia) 1349. If the patient cannot perceive the delivered modulation energy and if there is another amplitude to be tested 1350, then the clinician may incrementally increase the amplitude 1351. This process can continue until the patient indicates that the modulation energy is perceivable. If there are no other amplitudes to be tested at 1350, the clinician may determine that there is another pulse width to be tested at 1352, then increment the pulse width at 1353, and then deliver modulation at an initial amplitude at the incremented pulse width at 1348. The process may test multiple amplitudes 1350 and 1352 in a step-up manner until the patient perceives the delivery of the modulation energy. When the patient does perceive the delivery of the modulation energy at 1349 at the currently tested amplitude and pulse width, the amplitude may be recorded as the threshold for that pulse width and contact. It may be determined at 1354 whether there is another contact to be tested. Upon determining that there is another contact to be tested, a new contact is selected at 1355 and the process repeats for the newly-selected contact. Once every contact has been tested for every pulse width to be tested, then the calibration process may terminate at 1356. Since multiple amplitudes are tested for every contact and every tested pulse width at the contact, and since enough time has be given for the patient to perceive the modulation energy, this is a time-consuming process. Further, this process is inherently limited by the subjective nature of whether the patient perceives the modulation energy.

Figure 14:
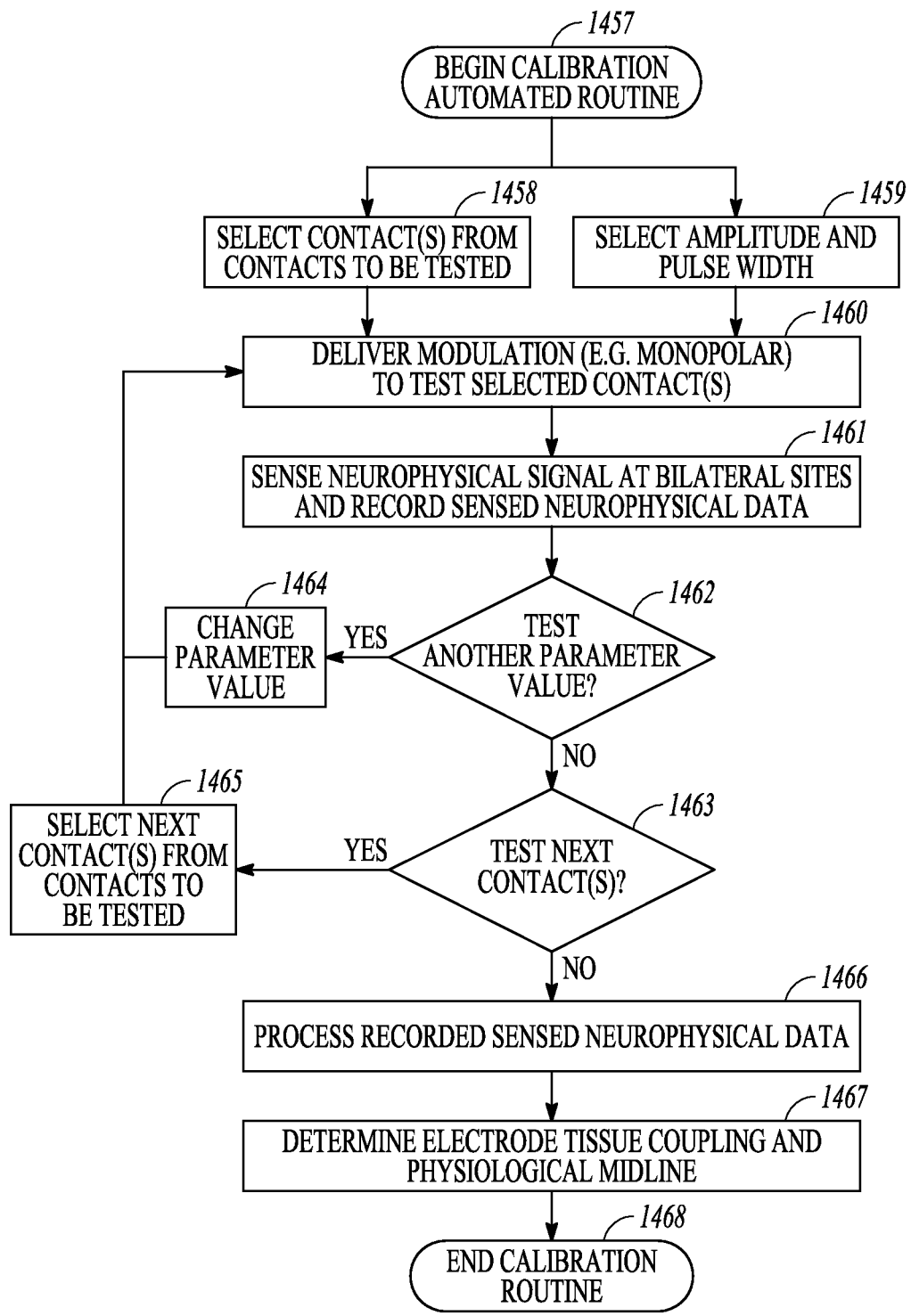
FIG. 14 illustrates, by way of example and not limitation, an automated, objective method for calibrating electrodes, according to various embodiments of the present subject matter.
Figure 15:
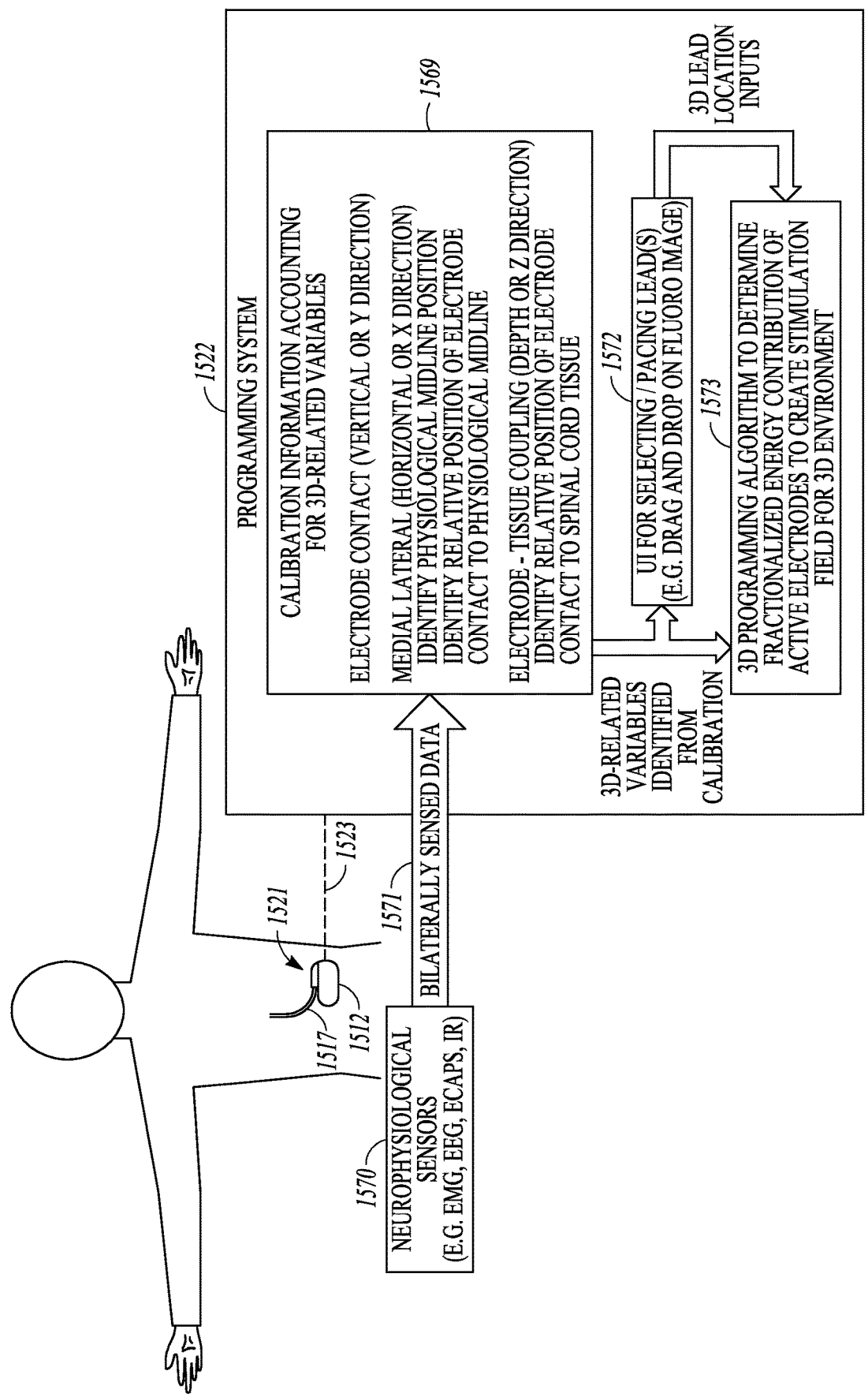
FIG. 15 illustrates, by way of example, a system for calibrating electrodes of neuromodulation device.

Various embodiments of the present subject matter provide an objective calibration of the electrodes both rostro-caudally and mediolaterally that enables accurate programming of the neuromodulation device. The objective calibration implemented by the present subject matter is faster than the subjective calibration that finds patient perception thresholds. FIG. 14 illustrates an automated, objective method for calibrating electrodes, according to various embodiments of the present subject matter. The automated process may be implemented using at least one processor of an external system (e.g. a programming system) to control a modulation device. The illustrated process may begin at 1457, and may select the electrode contact(s) to be tested 1458 and the modulation parameter values for use in delivering the modulation energy 1489. Some embodiments may test all electrode contacts on the lead(s), and some embodiments may test only some of the electrode contacts on the lead(s) such as, but not limited to every other electrode contact, every third electrode contact, or every fourth electrode contact. Some embodiments may quickly provide a first calibration by calibrating only some of the electrodes, and then provide a more robust calibration by calibrating all of the electrodes. For example, information obtained during the first calibration may be used to control the process used to calibrate all of the electrodes. At 1460, the modulation is delivered to test the selected contact(s). The modulation may be monopolar modulation using one electrode contact at a time, or using more than one electrode contact at a time. However, the present subject matter is not limited to monopolar modulation, as bipolar or multipolar modulation may be used during the calibration process. Further, various embodiments may specifically calibrate for cathodic modulation and/or anodic modulation. At 1461, the process senses a neurophysiological signal at bilateral sites. The sensors may be configured to sense somatosensory evoked potentials (SSEP) such as EEG, EMG, ECAPs, and the like. Some embodiments include only one type of sensor (e.g. EEG or EMG or ECAPs), and some embodiments include two or more types of sensors (e.g. EEG and EMG, or EMG and ECAPs, or EEG and ECAPs). Neurophysiological data (e.g. either the signal itself or data derived from the signal) may be recorded for analysis. Alternatively, the data may be analyzed in real-time or near real time as the neurophysiological signals are sensed. For example, some embodiments may transmit the neurophysiological data to an external system via Bluetooth or other communication technology for use by the external system to update the modulation parameters. In some embodiments, the neurophysiological data is derived from the signal using algorithm(s) to extract meaningful variables (e.g. amplitude, onset, frequency, and the like) from the signal. Sensing these signals at the bilateral sites allows the present subject matter to both determine the electrode-tissue coupling between the electrode and the spinal cord tissue, and to also determine the position of the physiological midline of the spinal cord. For example, the relative amplitude and/or onset of the sensed signals from laterally-positioned sensors may be used to determine the physiological midline. It is determined at 1462 whether another parameter will be tested, and at 1463 if other contact(s) will be tested 1463. The parameter value may be changed at 1464 and the next contact(s) to be tested may be selected at 1465, and modulation may be delivered again at 1460 and the neurophysiological signal can be sensed at bilateral sites 1461. Examples of parameters that may have different values tested using more than one parameter set may include but are not limited to pulse width, frequency, and burst duration. Since modulation signals having more complex patterns and shapes may be used, the system may be designed to calibrate the electrodes using different values or other differences in these patterns and/or shapes. Benefits of this automated process include objective measures of a sensed neurophysiological signal at bilateral sites that can be quickly obtained and used to determine the electrode-tissue coupling (e.g. depth with respect to the neuroanatomy or Z axis calibration for contact(s)) and determine a physiological midline of the spinal cord near the tested contact(s) (e.g. mediolateral position with respect to the neuroanatomy or X axis calibration for contact(s). FIG. 15 illustrates an example of a system for calibrating electrodes of neuromodulation device. The illustrated system is similar to the system illustrated in FIG. 5. The illustrated system 1520 includes an implantable system 1521, an external system 1522, and a telemetry link 1523 providing for wireless communication between implantable system 1521 and external system 1522. The implantable system 1521 includes an implantable modulation device (also referred to as an implantable pulse generator, or IPG) 1512, a lead system 1517. In some embodiments, the external system 1522 includes a programming system intended for a clinician or other caregiver to initialize and adjust settings for the implantable system 1521 and a remote control device intended for use by the patient. The illustrated programming system 1522 may include one or more devices which may include at least processor and instructions to implement a process 1569 such as is generally illustrated in FIG. 14, to determine calibration information account for three-dimensional variables for using the electrodes on the lead(s) to deliver modulation energy to the spinal cord. The selected electrode contact generally provides information related to the vertical or Y direction, the medial lateral information (horizontal or X direction) generally may be used to identify the physiological midline position and also identify the relative position of the physiological midline to the electrode contacts, and the electrode-tissue coupling (depth or Z direction) generally may be used to identify the relative position of the electrode contact to the spinal cord tissue, which accounts for variable distance between the electrode contact within the epidural space and the spinal cord tissue. Neurophysiological sensors 1570, such as electromyograms, electroencephalograms, evoked compound action potentials, infrared sensors, accelerometers, and the like, may be used to provide bilaterally sensed data 1571 to the programming system 1522 for use in the performing the calibration process 1569. In some embodiments, the programming system 1522 may derive 3D-related variables from the calibration process 1569. These 3D-related variables may provide functional and objective metrics for use in calibrating electric fields generated for SCS therapy. These variables may be provided to a user interface (UI) 1572 used to select and place leads (e.g. drag-and-drop) on a fluoro image of the spinal region. By way of example, a representation of the physiological midline of the spinal cord may be included in the image of the spinal cord and lead(s). An example of such an UI is Boston Scientific Neuromodulation Corporation's FluoroSync® system which allows leads to be selected and placed via drag-and-drop inputs on a display that mirrors the fluoro image. In some embodiments, the programming system 1522 may provide those variables to a 3D programming algorithm 1573 to determine fractionalized energy contribution of active electrodes to create desired stimulation fields for the 3D environment. An example of such an algorithm is Boston Scientific Neuromodulation Corporation's Illumina 3D™ which is designed to use "point and click" targeting to create customized stimulation fields to improve pain targeting by incorporating 3D environment. 3D lead location inputs may also be fed from the UI to the programming algorithm. More accurate location information with respect to the neuroanatomy promotes more accurate programming of the neuromodulation therapy.

Figure 16:
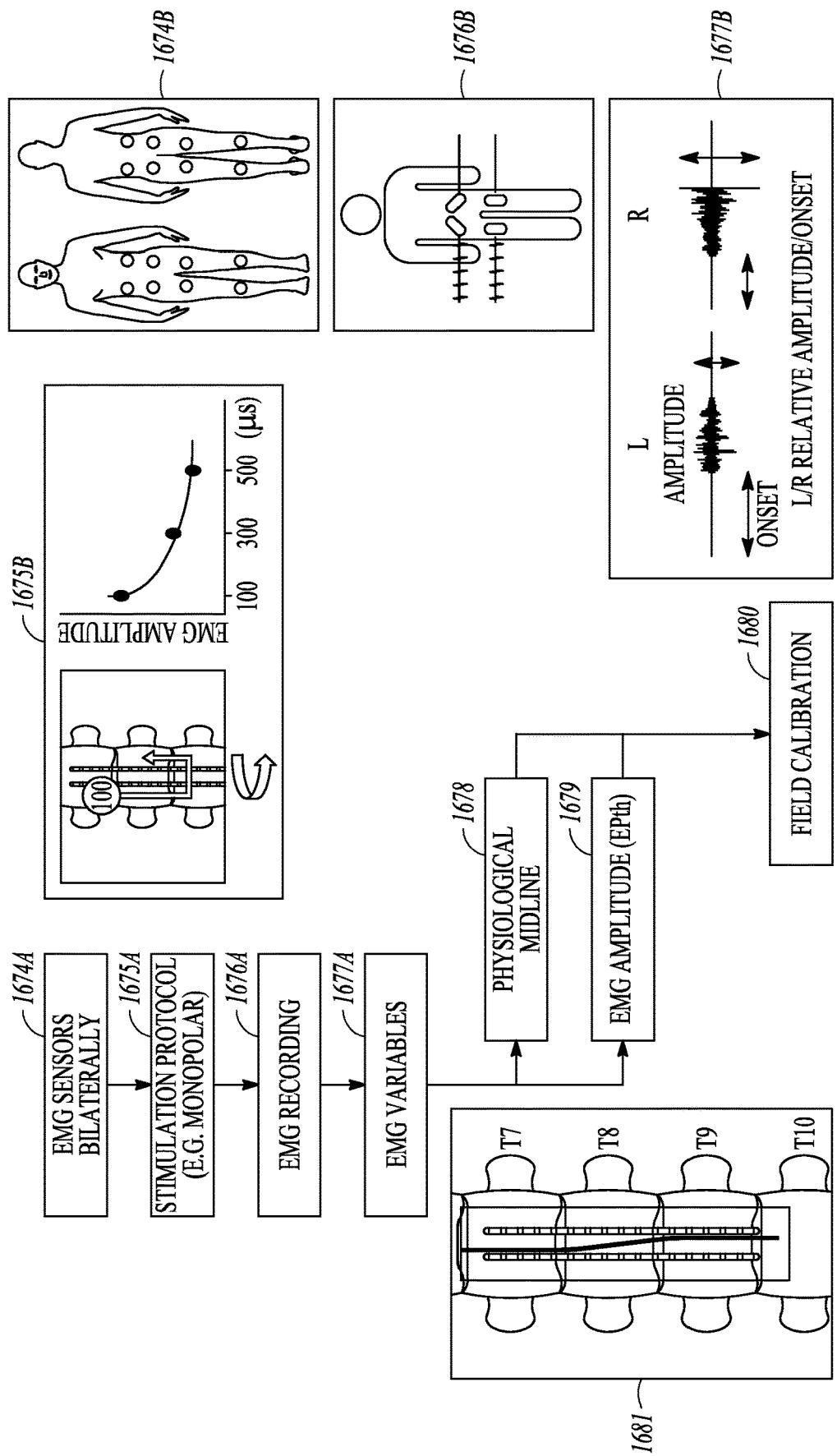
FIG. 16 illustrates, by way of example, a process for calibrating electrodes of a neuromodulation device using EMG sensors.

FIG. 16 illustrates, by way of example and not limitation, a process for calibrating electrodes of a neuromodulation device using EMG sensors. EMG sensors may be used to detect the muscle twitches that are elicited by the neuromodulation. At 1674A and 1674B, EMG sensors may be bilaterally placed on the patient. For example, the EMG sensors may be patches configured to be externally placed on the patient. The illustration at 1674B illustrates patches bilaterally placed (left/right) on both the front and back of the patient. At 1675A and 1675B, the stimulation protocol is implemented. For example, some embodiments deliver monopolar neuromodulation to calibrate electrode contacts. Some embodiments test more than one value of a modulation parameter. For example, 1675B illustrates that duty cycles of a signal may be tested with different pulse widths (e.g. 100 µs, 300 µs and 500 µs), and further illustrates that a curve fitting technique may be implemented to interpolate calibration results for other pulse widths. At 1676A and 1676B, the bilaterally-sensed EMG signals may be recorded. The EMG signals may be processed at 1677A and 1677B to derive EMG variables. For example, the derived EMG variables may include an amplitude for each side of the bilaterally-positioned sensors, and may include onset information which indicates a time delay before the modulation energy. These values may be absolute values ore relative values with respect to each other. Based on these derived EMG variables, the system is able to determine the physiological midline (X-direction information) and the EMG amplitude indicative of electrode-tissue coupling (Z-direction information). This information may be used to perform field calibration 1680 (e.g. program fractionized values to produce a desired field) and/or illustrate a midline on a user interface 1681. For example, the field calibration may receive the information as inputs to a field element model of the spinal cord. The information provides more accurate inputs into the field model, which enables more precise targeting of neural tissue. By way of example and not limitation, some embodiments may target the dorsal column, some embodiments may target the dorsal horn, some embodiments may target the dorsal root, and some embodiments may target the dorsal root ganglia. The modulation field of the targeted region may be designed to enhance the neural activity in the targeted region or may be designed to inhibit or block the neural activity in the targeted region.

Figure 17:
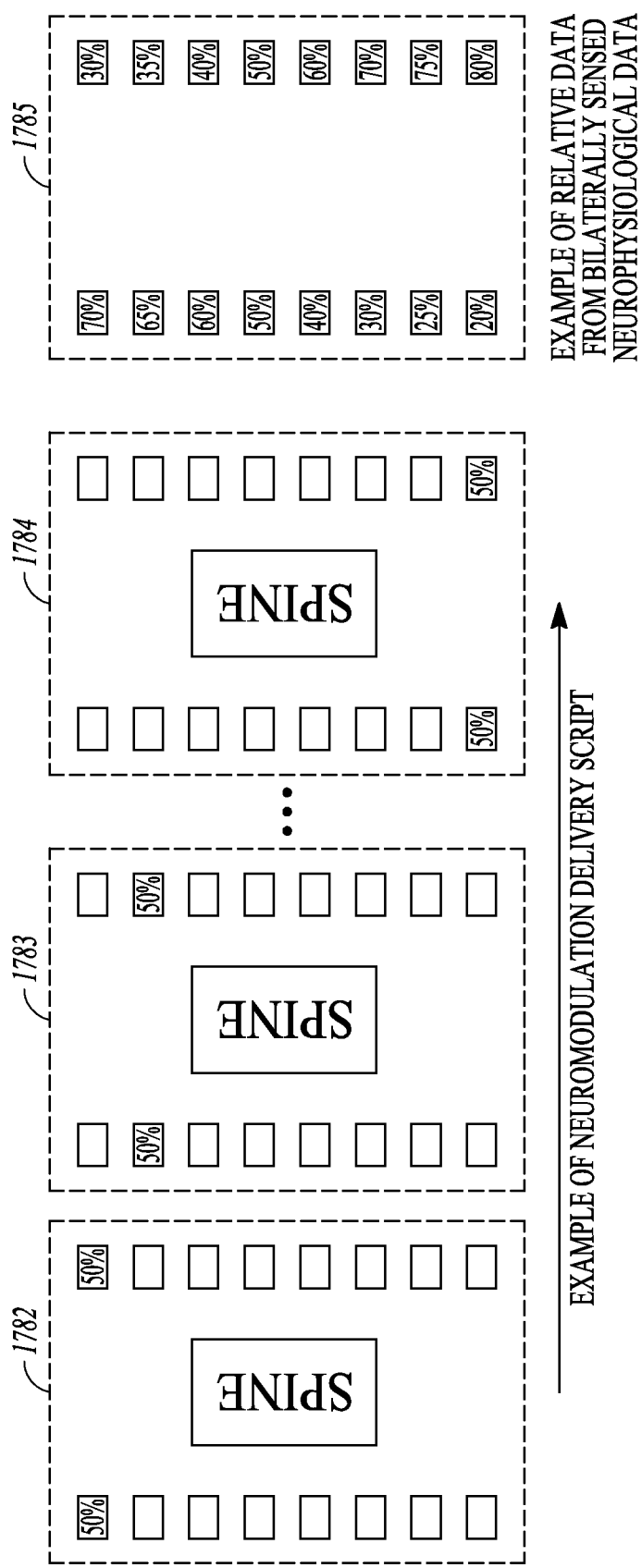
FIG. 17 illustrates an example of a neuromodulation deliver script and relative data that may be derived from bilaterally sensed neurophysiological data.

FIG. 17 illustrates an example of a neuromodulation deliver script and relative data that may be derived from bilaterally sensed neurophysiological data. The illustrated example includes two 8-electrode leads bilaterally placed along the spine. By way of example, some embodiments may deliver an equal amount of energy to each of two bilateral electrodes, one level at a time. For example, 50% of the delivered energy may be provided to the first electrode in both leads as illustrated at 1782, and then to the second electrode in both leads as illustrated at 1783, and so on until 50% of the delivered energy may be provided to the eighth electrode in both leads as illustrated at 1784. Some embodiments may deliver 100% to one of the two electrode contacts, and then 100% to the other of the two electrode contacts. Other scripts may be implemented. At each level where the energy is delivered, neurophysiological signals are bilaterally sensed and recorded for each of the electrodes. For example, the amplitude of the signal may be used to determine how much of the delivered energy is causing the physiological effect on the left side and how much of the delivered energy is causing the physiological effect on the right side. For example, when the first level of electrodes are used to deliver the modulation energy at 1782 using equally-distributed energy, the observed effect based on the bilaterally-sensed neurophysiological signal may be determined to be 70% on the left and 30% on the right side. This process may continue for each level of electrodes, and this information may be used to determine both the midline (mediolateral information—X axis), and the electrode tissue-coupling (Z axis) based on the magnitude of the sensed signals. A simple representation of a midline is illustrated in 1785.

Figure 18:
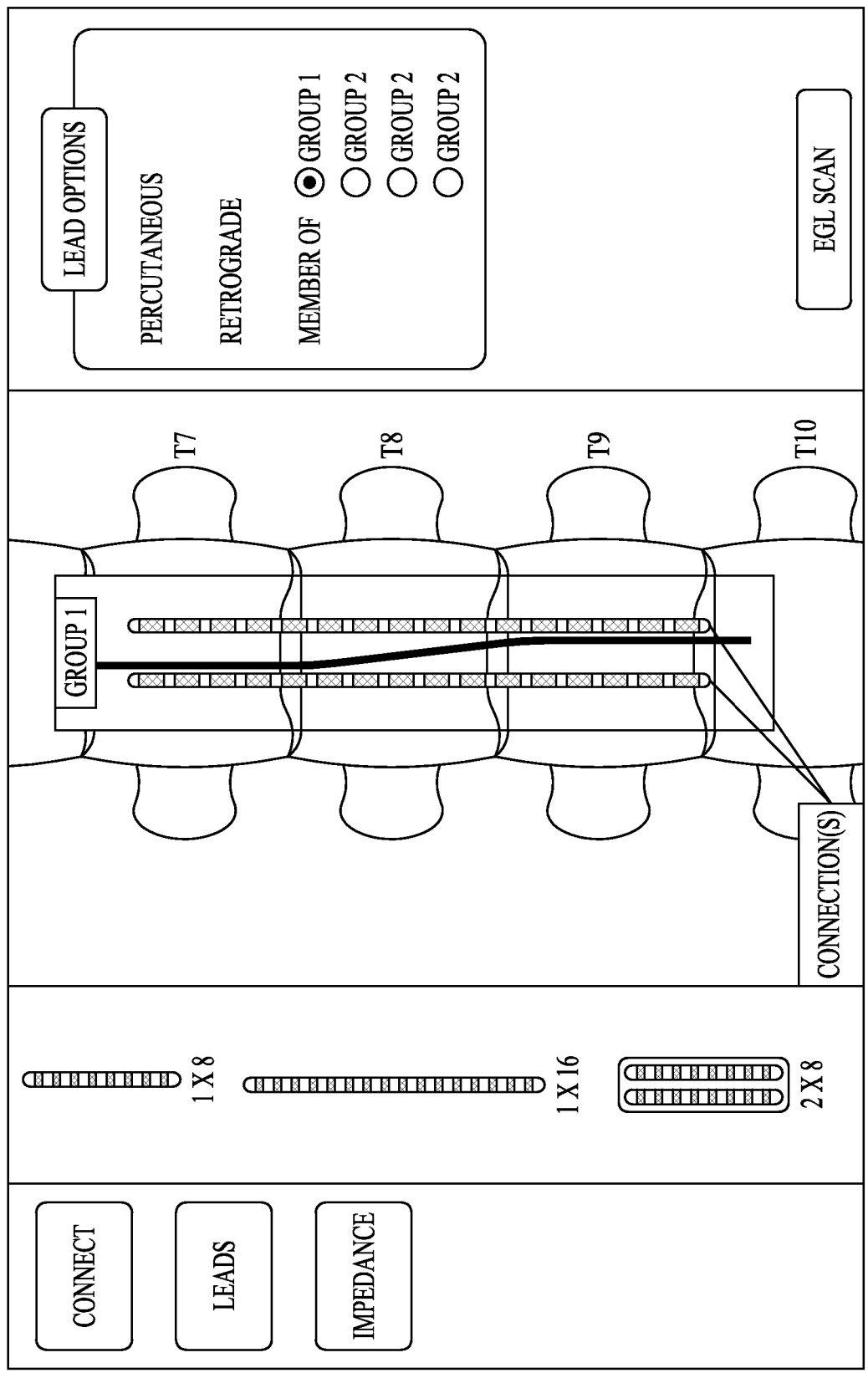
FIG. 18 illustrates, by way of example, a user interface that presents a fluoro image to a clinician, and also allows the clinician to drag-and-drop a selected lead into position on the fluoro image.

As was generally illustrated at 1572 in FIG. 15, the 3D related variables identified from the calibration may be provided to the user interface. FIG. 18 illustrates, by way of example and not limitation, an example of a user interface that presents a fluoro image to a clinician, and also allows the clinician to drag-and-drop a selected lead into position on the fluoro image. The at least one processor of the programming system may determine 3D position information for the electrodes using the UI. Further, the midline determined during the calibration process may be presented on the UI.

As was generally illustrated at 1573 in FIG. 15, the 3D related variables identified from the calibration may be provided to a 3D programming algorithm to determined fractionalized energy contributions. FIGS. 19-32F illustrate examples of the algorithm and examples of fractionalizations that may be determined using the algorithm.

Figure 19:
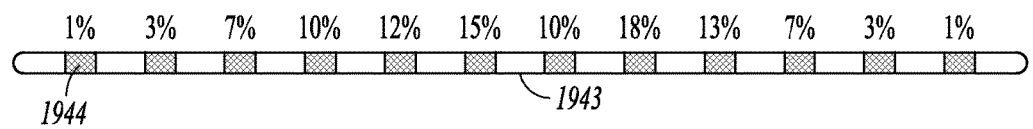
FIG. 19 is a schematic view of the electrical modulation lead showing an example of the fractionalization of the anodic current delivered to the electrodes on the electrical modulation lead.
Figure 20:
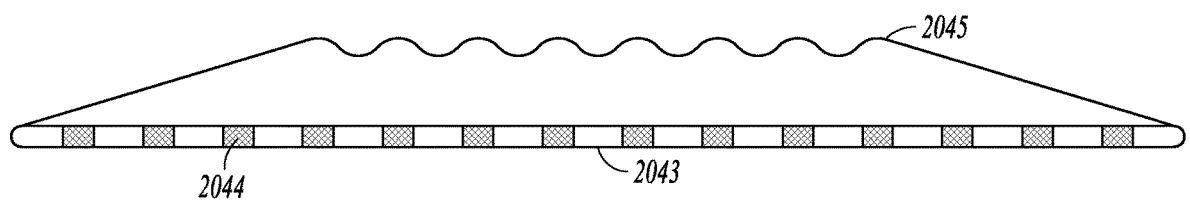
FIG. 20 illustrates, by way of example, a schematic illustration of a gradient in the longitudinal direction along the axis of the electrical modulation lead.
Figure 21:
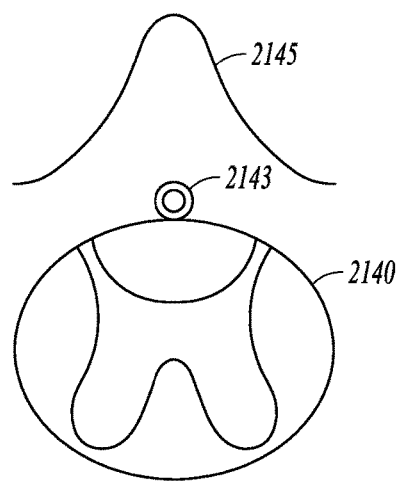
FIG. 21 illustrates, by way of example, a schematic illustration of a gradient in the transverse direction.

FIG. 19 is a schematic view of the electrical modulation lead 1943 showing an example of the fractionalization of the anodic current delivered to the electrodes on the electrical modulation lead. In order to provide a simpler illustration, these figures illustrate fractionalization using monopolar modulation where a case electrode of the waveform generator is the only cathode, and carries 100% of the cathodic current. The fractionalization of the anodic current shown in FIG. 19 does not deliver an equal amount of current to each electrode 1944, because this embodiment takes into account electrode/tissue coupling differences, which are the differences in how the tissue underlying each electrode reacts to electrical modulation. This may account for, among other things, the distance from the electrode to the targeted tissue and conductivity of the tissue between the electrode and targeted tissue. The magnitude of the electrical field tapers down at the ends of the electrical modulation lead. Fractionalization of the current to the electrodes is controlled such that the tissue underlying each electrode in the middle portion of the electrical modulation lead reacts approximately equally to the electrical modulation, or tissue activation underlying each electrode are eliminated. However, the resulting fractionalization is not equal. In the embodiment shown in FIG. 19, fractionalization of the current to the middle electrodes varies from 10% to 18%, reflecting the variation in the tissue underlying those electrodes. The fractionalization across the electrical modulation lead can vary in any manner as long as the total of fractionalized currents equals 100%. Various embodiments described herein implement a programmed algorithm to determine the appropriate fractionalization to achieve a desired modulation field property (e.g. constant electric field, or constant electric field magnitude, or constant voltage). FIG. 20 illustrates, by way of example, a schematic illustration of a gradient in the longitudinal direction along the axis of the electrical modulation lead. The electrical field strength 2045 in the longitudinal direction is plotted over a schematic representation of the electrodes 2044 on the electrical modulation lead 2043. The illustration in FIG. 20 shows that the electrical field strength is substantially constant over the middle portion of the electrical modulation lead, but may form a wave with very small amplitude because of the gaps between the electrodes in the lead. This substantially constant electrical field forms a small longitudinal gradient, which minimizes activation of the large myelinated axons in the dorsal column. The illustration in FIG. 20 also shows the electrical field in the longitudinal direction tapering at the ends of the electrical modulation lead. FIG. 21 illustrates, by way of example, a schematic illustration of a gradient in the transverse direction. The transverse electrical field strength 2145 in the transverse direction is plotted over a schematic representation of the electrical modulation lead 2143 and the spinal cord 2140 of the patient. The illustration in FIG. 21 shows that the transverse electrical field strength is greatest adjacent the electrical modulation lead and falls off lateral of the electrical modulation lead. Use of additional modulation leads to widen the electrode array may be used to provide desired fractionalization to also provide a region of a substantially constant electric field for a distance along the transverse direction. Substantially constant electric fields favor modulation of dorsal horn and/or dorsal root neuronal elements over dorsal column neuronal elements. Various embodiments use a substantially constant electric field to target inhibitory interneurons that propagate in an anterior-posterior direction.

Modulation thresholds vary from patient to patient and from electrode to electrode within a patient. An electrode/tissue coupling calibration of the electrodes may be performed to account for these different modulation thresholds and provide a more accurate fractionalization of the current between electrodes. For example, as was illustrated and discussed with respect to FIG. 13, perception threshold may be used to normalize or calibrate the electrodes. Examples of other patient-perceived indicators may include temperature, proprioception, general discomfort, pressure, itch, pulling, vibration and the like. The system may be configured to calibrate therapy using a threshold for the patient to perceive the modulation or a threshold for the patient to tolerate the modulation or another perceived range of modulation intensity. According to various embodiments of the present subject matter, sensors are used to bilaterally sense neurophysiological signals. Examples of sensors include that may be used for the bilateral sensing may include electromyograms (EMGs), quantitative sensory testing (QST), electroencephalogram (EEG), electrocorticogram (ECoG), diffuse optical imaging, functional magnetic resonance imaging (fMRI), local field potentials (LFPs) in axons, evoked compound action potentials (eCAPs) in axons.

Various embodiments of the present subject matter may use "target multipoles" to provide a linear field that may maximize the electric field in a region while minimizing the activation of dorsal columns. These target multipoles may be referred to as "ideal" or "virtual" multipoles. Each target pole of a target multipole may correspond to one physical electrode, but may also correspond to a space that does not correspond to one electrode, and may be emulated using electrode fractionalization. Target multipoles are briefly described herein.

A stimulation target in the form of a target poles (e.g., a target multipole such as a target bipole or target tripole or a target multipole with more than three target poles) may be defined and the stimulation parameters, including the fractionalized current values on each of the electrodes, may be computationally determined in a manner that emulates these target poles. Current steering may be implemented by moving the target poles about the leads, such that the appropriate fractionalized current values for the electrodes are computed for each of the various positions of the target pole.

With reference to, the CP may be configured to accept relative electrode positions and a representation of an target electrical field (instead of including these parameters in the design of navigation tables) and map the target electrical field to the electrodes to thereby yield the polarities and percentages of electrical current to be associated with the electrodes, as well as a boost or scaling factor for globally adjusting the magnitude of the total current supplied to the electrodes. Electrode locations and information about the desired electrical field may be independently inputted into the algorithm. As discussed and illustrated with respect to FIG. 15, 3D-related variables from the calibration of the electrodes may be inputted into the algorithm.

Figure 22:
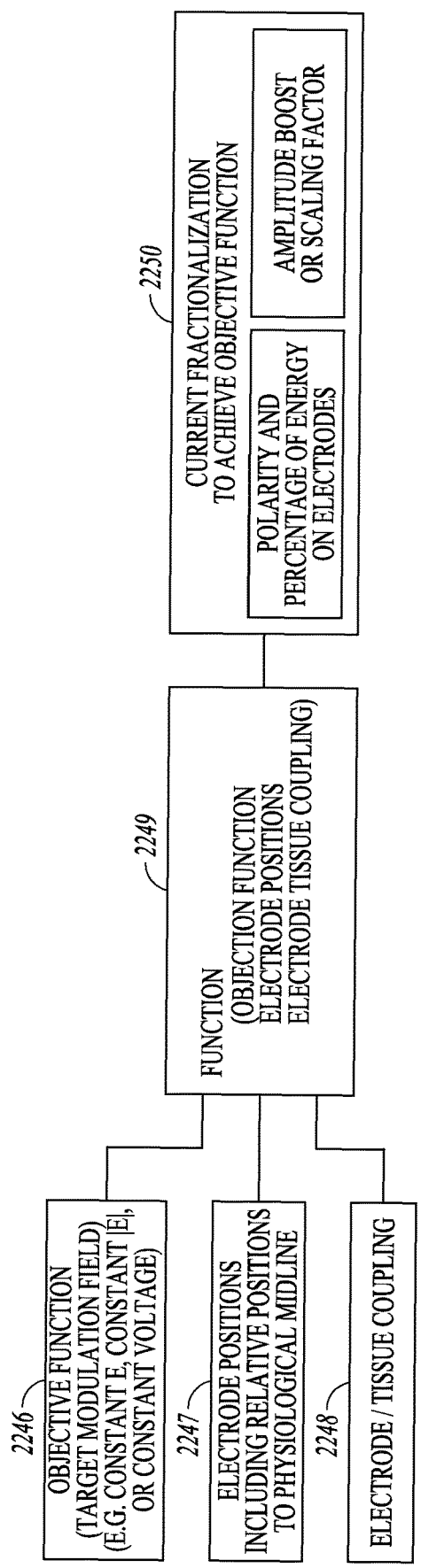
FIG. 22 illustrates, by way of example, an embodiment for determining fractionalization to achieve an objective function.

FIG. 22 illustrates, by way of example, an embodiment for determining fractionalization to achieve an objective function. An objective function refers to a function with desirable characteristics for modulating the targeted tissue. The objective function may also be referred to as an objective target function. An objective function 2246 for a broad and uniform modulation field is identified for a given volume of tissue. Examples of an objective function includes a constant E (electric field), a constant |E| (electric field magnitude), and a constant voltage. The lead and electrode configuration 2247, including relative positions to a physiological midline, are also identified, as well as electrode tissue coupling 2248. A function 2249 is performed that is dependent on the objective function, the electrode positions, and the electrode tissue coupling. The result of the function is the fractionalization of modulation energy (e.g. current) 2250 for each electrode to achieve the objective function. The fractionalization of modulation energy may be expressed, for each electrode, as a polarity (e.g. cathodic or anodic) and percentage of the total cathodic energy or total anodic energy delivered to the plurality of electrodes on the lead at a given time. Furthermore, an amplitude boost or scaling factor may be applied to the fractionalization values.

Figure 23:
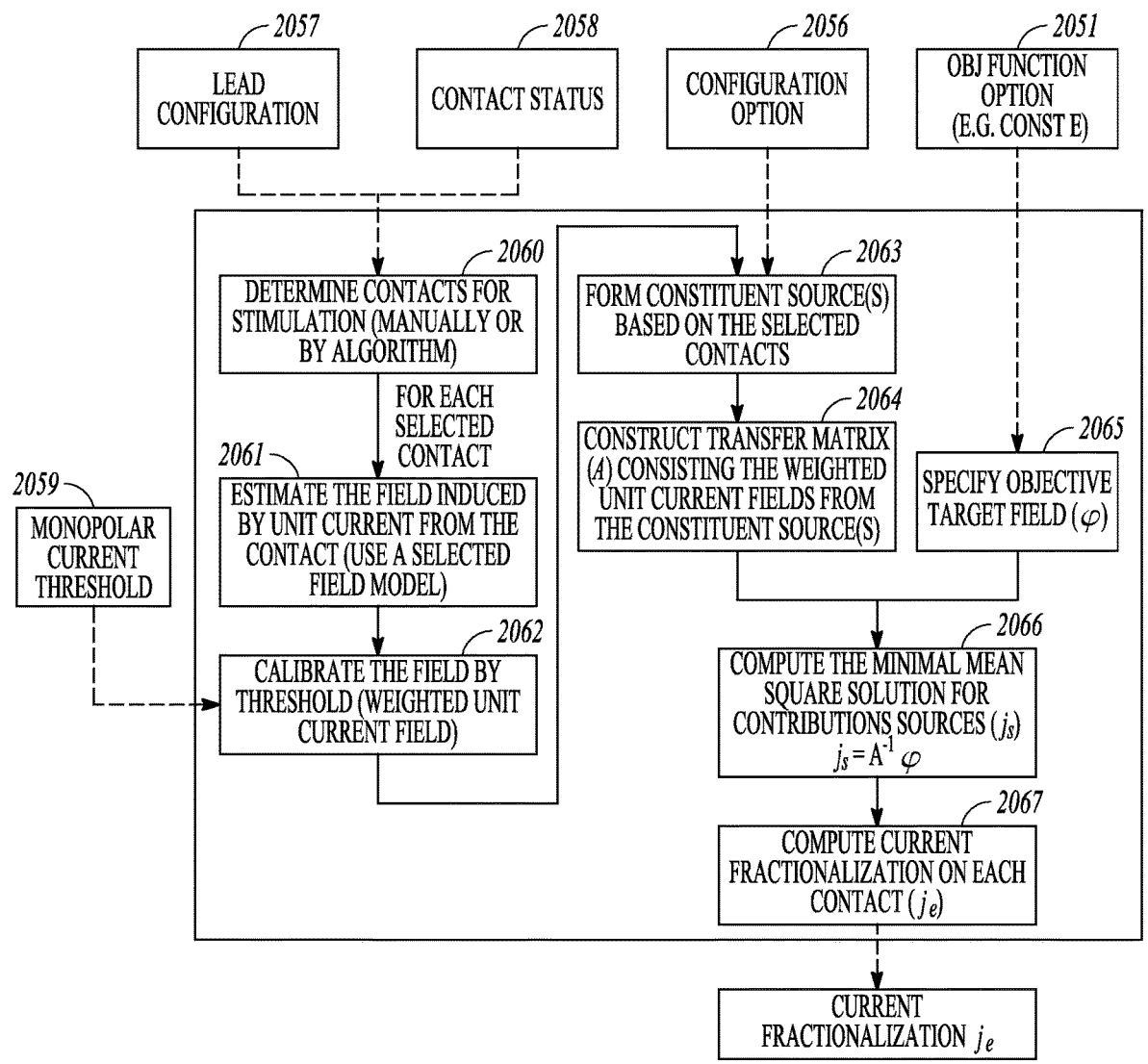
FIG. 23 illustrates, by way of example, an embodiment for determining fractionalization to achieve an objective function with more detail.

FIG. 23 illustrates, by way of example, an embodiment for determining fractionalization to achieve an objective function with more detail. An objective target function 2351 (e.g. constant E) is provided as an input to a process. Other inputs to the process include a configuration option 2356, a lead configuration 2357 and electrode contact status 2358, and a threshold 2359 such as a current threshold or more particularly a monopolar current threshold.

The lead configuration 2357 and contact status 2358 identify an electrode arrangement, identifying a position of each electrode to determine the field. The overall field is a superimposed field from each electrode. The configuration option 2356 refers to monopolar (same polarity for all activated electrodes) and multipolar options (combined anode and cathodes in field). The threshold is used to compensate for electrode/tissue coupling differences.

The contacts for stimulation may be determined automatically or manually 2360 from the lead configuration and contact status. A selected field model may be used to estimate the field induced by unit current from the contact 2361. The field is calibrated using the threshold 2362. For example, the unit current field may be weighted. Constituent forces are formed based on the selected contacts 2363, and a transfer matrix 2364 is constructed for use to compute the minimal mean square solution 2366 using contributions from the constituent sources and using a specified target field 2365. The solution can be used to compute the current fractionalization on each contact 2367.

With reference to FIGS. 24A-24B, the CP may map a target electrical field to the electrode array by estimating the field potential values (or some other linear electrical parameter, such as an activating function, current density, etc.) of the target field at a plurality of spatial observation points. The CP may accomplish this by determining the desired locations of target current source poles relative to the electrode array, and modeling an electrical field generated by the target current source poles to determine desired field potential values at the spatial observation points (e.g., using analytical and/or numerical models).

Although target current source poles are one way to represent a "target electrical field", other representations of target fields may be used. The locations of the target current source poles may be determined in a manner that places the resulting electrical field over an identified region of the patient to be stimulated. The spatial observation points may be spaced in a manner that would, at the least, cover the entire tissue region to be stimulated and/or would not cover a tissue region that should not be stimulated. The locations of the target current source poles may be defined by the user, and may be displayed to the user along with the electrode locations, which as briefly discussed above, may be determined based on electrical measurements taken at the electrodes. Referring to FIGS. 25A-25C, the CP may select, or allow a user to select, a plurality of constituent current sources at the locations of the electrodes. The locations of the electrodes may be determined based on measurements taken at the electrodes in response to sub-threshold electrical signals transmitted between the electrodes. In the illustrated target bipole a first constituent current source can be defined at the locations of electrodes E1 and E2 as −100% and +100%, respectively (FIG. 25A); a second constituent current source can be defined at the locations of electrodes E2 and E3 as −100% and +100%, respectively (FIG. 25B); a third constituent current source can be defined at the locations of electrodes E3 and E4 as −100% and +100%, respectively (FIG. 25C); and so on. The location of each of the electrodes is included within at least one of the constituent sources. Thus, the minimum number of constituent sources may be equal to the number of contacts less one, or may equal the number of contacts (e.g., if a monopole is used as the constituent source).

Once the constituent sources are selected, the CP may determine the relative strengths of the constituent current sources that, when combined, result in estimated electrical field potential values at the spatial observation points that best matches the desired field potential values at the spatial observation points. In particular, the CP may model the constituent current sources (e.g., using analytical and/or numerical models) and estimate the field potential values per unit current (V/mA) generated by each of the constituent current sources at the spatial observation points, and may generate an m×n transfer matrix (shown in FIG. 26) from the estimated field potential values per unit current, with m equaling the number of spatial observation points and n equaling the number of constituent sources. The relative strengths of the constituent current sources may be determined using an optimization function that includes the transfer matrix A and the desired field potential values.

The optimization function may be a least-squares (overdetermined) function expressed as: $|\varphi - A\hat{j}|^2$, where $\varphi$ is an m-element vector of the desired field potential values, A is the transfer matrix, and $\hat{j}$ is an n-element vector of the strengths of the constituent current sources. The constituent current source strengths $\hat{j}$ may be solved such that the optimization function $|\varphi - A\hat{j}|^2$ is minimized. The square difference is minimized if $\varphi=A\hat{j}$. One approach for solving this problem may be to invert the transfer matrix A and pre-multiply, such that $A^{-1}=\varphi A^{-1}A\hat{j}$, which yields the solution $\hat{j}=A^{-1}\varphi$. Once the strengths of the constituent current sources are determined, the CP converts these strengths to current distributions on the electrodes in the form of a polarity and percentage.

The remainder of this document discusses various embodiments that relate to enhancing the effectiveness a modulation field such as a sub-perception modulation field, various embodiments that relate to the electrode selection and refinement for use in delivering a modulation field such as a sub-perception field. The effectiveness of these enhancements are further enhanced by the accurate calibration of the electrodes in the medial lateral direction with respect to a determined midline and by the electrode-tissue calibration coupling. These embodiments may be implemented separately, or may be implemented in various combination(s). Such combination(s) may be useful for delivering sub-perception modulation of the DH or DR tissue over DC tissue. However, some embodiments may be used to deliver other modulation therapies.

Neural tissue in the region of the spinal cord has different characteristics. For example, DC fibers (mostly myelinated axons) run in an axial direction, whereas DH (e.g. neuronal cell terminals, neuronal cell bodies, dendrites, and axons) fibers are oriented in many directions. The distance from typically-placed epidural SCS leads to DH fibers are different than the distance from these leads to DC fibers. Further, DH fibers and dorsal column fibers have different responses (e.g. activation functions) to electrical modulation. The strength of modulation (i.e., depolarizing or hyperpolarizing) of the DC fibers and neurons is described by the so-called "activation function" which is proportional to the second-order spatial derivative of the voltage along the longitudinal axis of the spine ($\partial\,2V/\partial\,x2$). This is partially because the large myelinated axons in DC are primarily aligned longitudinally along the spine. On the other hand, the likelihood of generating action potentials in DH fibers and neurons is described by an activating function that is proportion to the first-order spatial derivative of the voltage along the spine ($\partial\,V/\partial\,x$), which is otherwise known as the electric field. Thus, the DH activating function is proportional to the first-order derivative of the voltage along the fiber axis, whereas the DC activating function is proportional to the second-order derivative of the voltage along the fiber axis. Accordingly, the distance from the electrical field locus affects the DH activating function ($\partial\,V/\partial\,x$) less than it affects the dorsal column activating function $\partial\,2V/\partial\,x2$. The neuronal elements (e.g., neurons, dendrites, axons, cell bodies, and neuronal cell terminals) in the DH can be preferentially stimulated over the DC neuronal elements by minimizing the longitudinal gradient of an electrical field generated by a neuromodulation lead along the DC, thereby providing therapy in the form of pain relief without creating the sensation of paresthesia. This technique relies, at least partially on the natural phenomenon that DH fibers and DC fibers have different responses (activation functions) to electrical modulation.

Various embodiments for enhancing modulation field selectively modulate DH and/or DR tissue over DC tissue. Conventional SCS activates DC fiber axons, and the orthodromic propagation of action potentials induces perception of paresthesia in the brain and antidromic propagation of action potentials to fiber collaterals and terminals ending in DH evokes pain control mechanism in DH. Various embodiments shape the stimulation field to preferably stimulate fiber terminals ending in DH and/or DR to provide pain relief without inducing paresthesia. For example, uniformity in a first order gradient of voltage (i.e. uniformity in electric field) may be more efficient in stimulating DH fiber terminals and/or stimulating DR fibers. Uniformity across a larger field may eliminate the needs for searching optimal stimulation site and create broader coverage of pain. For example, the uniformity may extend between or among two or more electrodes within an arrangement of electrodes. In other examples, the uniformity may extend among three, four, five, six or more electrodes within an arrangement of electrodes to eliminate the needs for searching for an optimal simulation site and creating a broader therapeutic coverage. Thus, the uniformity extends over a substantial portion of the lead. Some embodiments are configured to determine a modulation parameter set to create a field shape to provide a broad and uniform modulation field to enhance modulation of targeted neural tissue (e.g. DH tissue or DR tissue). Some embodiments are configured to determine a modulation parameter set to create a field shape to reduce or minimize modulation of non-targeted tissue (e.g. DC tissue).

Various embodiments disclosed herein are directed to shaping the modulation field to enhance modulation of some neural structures and diminish modulation at other neural structures. The modulation field may be shaped by using multiple independent current control (MICC) or multiple independent voltage control to guide the estimate of current fractionalization among multiple electrodes and estimate a total amplitude that provide a desired strength. For example, the modulation field may be shaped to enhance the modulation of DH neural tissue and to minimize the modulation of DC tissue. A benefit of MICC is that MICC accounts for various in electrode-tissue coupling efficiency and perception threshold at each individual contact, so that "hot-spot" stimulation is eliminated.

The modulation field may be shaped to provide a constant electric field (E) at the DH tissue in a selected direction. The electric field (E) at the DH in any direction is the negative gradient (negative rate of change) of the scalar potential field (V) in that direction. Due to the linearity of field superposition, a transfer function can be formed to estimate the EDH(x,y,z) at selected direction induced by unit current from a single electrode located at (x0, y0, z0), the total E field is the linear combination of the E field induced by currents from each active electrode weighted by the current fractionalization. In an example, the modulation field may be a constant V field along the DC tissue.

Due to the linearity of field superposition, a transfer function can be formed to estimate the VDC(x,y,z) at selected direction induced by unit current from a single electrode located at (x0, y0, z0), the total V field is the linear combination of the V field induced by currents from each active electrode weighted by the current fractionalization.

Various embodiments may design a field to maximize the linear progression of extracellular voltages in the rostral-caudal direction for subthreshold and suprathreshold activation of terminals oriented in the anterior posterior (AP) direction. Various embodiments of the present subject matter produce a linear field by stacking fractionalizations of target poles in a directional, progressive manner as generally discussed with respect to FIGS. 27A-27E by way of example and not limitation.

Figure 27A:
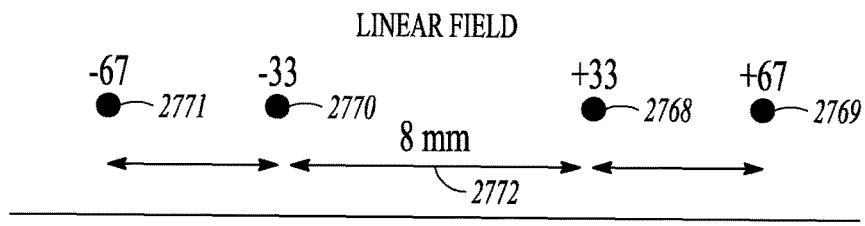
FIG. 27A illustrates an embodiment of to target multipole that includes fractionalized target anodes and fractionalized target cathodes.

More particularly, FIG. 27A illustrates an embodiment of a target multipole that includes fractionalized target anodes and fractionalized target cathodes designed to maximize the electric field in a region while minimizing the "activating function" (i.e. activation of dorsal columns, axons of passage) represented by the second difference of the extracellular potentials generated by a field. The target multipole illustrated in FIG. 27A progressively stacks fractionalization of target poles. The illustrated target multipole may be referred to as a base field design, as it may serve as a base from which the field length, width and orientation may be adjusted, and as a base from which features such as flanking electrodes may be added. In the illustrated embodiment, the target multipole includes first and second target anodes where in the first target anode 2768 represents 33% of the total anodic current and the second target anode 2769 represents 67% of the total anodic current; and further includes first and second target cathodes where in the first target cathode 2770 represents 33% of the total cathodic current and the second target anode 2771 represents 67% of the total cathodic current. Other percentages may be used to progressively increase the percentage moving away from the center of the target multipole and/or to alter the length of the target field. Some embodiments may include more than two target anodes in which the percentage of anodic current progressively increases away from the center of the target multipole. Some embodiments may include more than two target cathodes in which the percentage of cathodic current progressively increases away from the center of the target multipole. Some embodiments may include one target anode (100%) and more than one target cathode. Some embodiments may include one target cathode (100%) and more than one target anode.

Some embodiments of the target multipole may include a center 2772 of the target multipole, a first target anode 2768 and a second target anode 2769 on an anodic side of the center of the target multipole, and a first target cathode 2770 and a second target cathode 2771 on an opposing cathodic side of the center of the target multipole. The first and second target anodes, the center, and the first and second target cathodes may be in-line with each other. The first target anode and the first target cathode may have equal fractionalization magnitudes (e.g. 33% of the total anodic or cathodic current), and the second target anode and second target cathode may have equal fractionalization magnitudes (e.g. 67% of the total anodic or cathodic current). By way of example and not limitation, a shorter target multipole may have target poles with fractionalizations of 75/25/−25/−75 and a longer target multipole may have target poles with fractionalizations of 55/33/11/−11/−33/−55.

The distances from the first target anode to the center and from the first target cathode to the center may be equal. For example, the distance between the first target anode to the first target cathode is illustrated to be 8 mm. The distance between the first target anode to the center may be 4 mm, and the distance between the first target cathode to the center may be 4 mm. Similarly, distances from the second target anode to the center and from the second target cathode to the center may be equal (e.g. 8 mm). It is noted that the present subject matter may be implemented using other electrode spacings. Furthermore, if the spinal and electrode geometry are accounted for, the fractionalization magnitudes and the distances between the target poles may be unequal.

In some embodiments, the distances from the second target anode to the first target anode may be 4 mm, from the first target anode to the center may be 4 mm, from the center to the first target cathode may be 4 mm, and from the first target cathode to the second target cathode may be 4 mm. Thus, the distance of the second target cathode from the center may be twice the distance of the first target cathode form the center, and the distance of the second target anode from the center may be twice the distance of the first target anode from the center. The fractionalization magnitude of the second target cathode may be twice the fractionalization magnitude of the first target cathode, and the fractionalization magnitude of the second target anode may be twice the fractionalization magnitude of the first target anode.

Figure 27B:
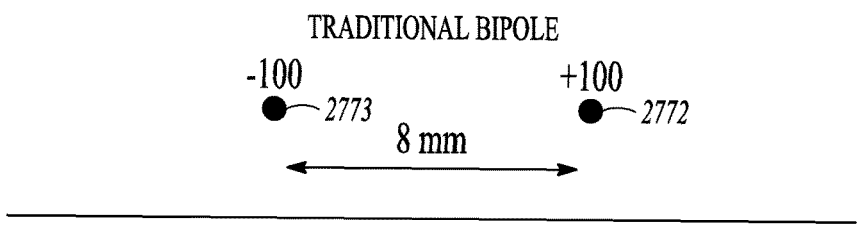
FIG. 27B illustrates a traditional bipole.
Figure 27C:
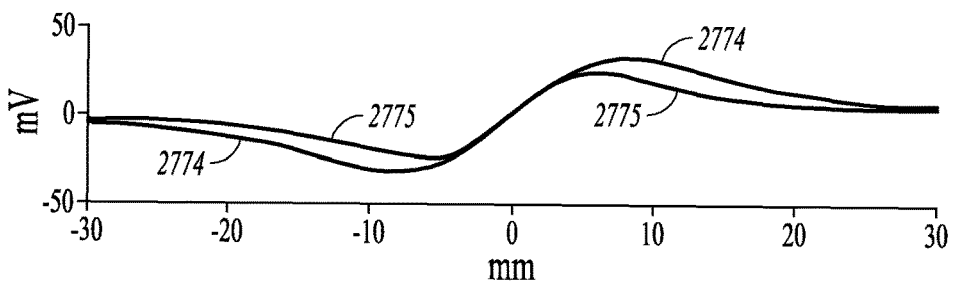
FIG. 27C compares a target multipole voltage and a bipole voltage.

The field design for the target multipole illustrated in FIG. 27A may be compared to a traditional bipole, illustrated in FIG. 27B, which has one anode 2772 and one cathode 2773. FIG. 27C compares a target multipole voltage 2174 in mV over the length of the base field design illustrated in FIG. 27A and a bipole voltage 2775 in mV over the length of the traditional bipole illustrated in FIG. 27B. As illustrated in FIG. 27C, the target multipole voltage 2774 has larger amplitude and a wider wave shape than the bipole voltage 2775.

Figure 27D:
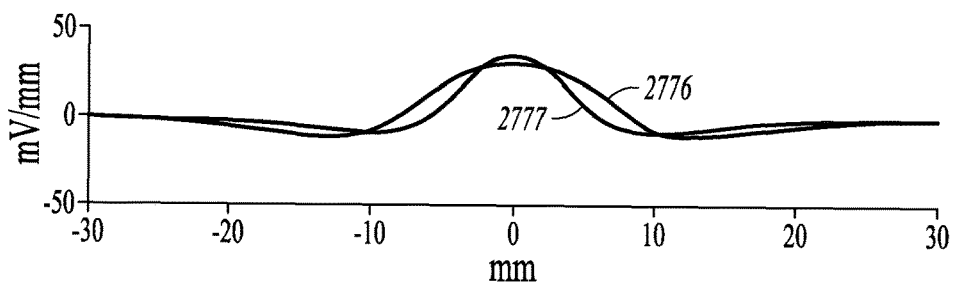
FIG. 27D compares a target multipole voltage per distance (electric field) and a bipole voltage per distance (electric field)

FIG. 27D compares a target multipole voltage per distance 2776 (first order spatial derivative of the voltage or "electric field") in mV per mm over the length of the base field design illustrated in FIG. 27A and a bipole voltage per distance 2777 (first order spatial derivative of the voltage or "electric field") in mV per mm over the length of the traditional bipole illustrated in FIG. 27B. As illustrated in FIG. 27D, the target multipole voltage per distance 2776 has only a slightly smaller peak voltage amplitude bipole voltage per distance 2777 but a wider field as it has a larger amplitude at −8 mm and 8 mm, for example. Thus, the base field design of FIG. 27A increases the electric field and the extent of the electric field in comparison to traditional bipole of FIG. 27. As stated previously, DH fibers have an activating function proportional to the electric field, so it is desirable to increase the electric field and the extent of the electric field to modulate DH fibers.

Figure 27E:
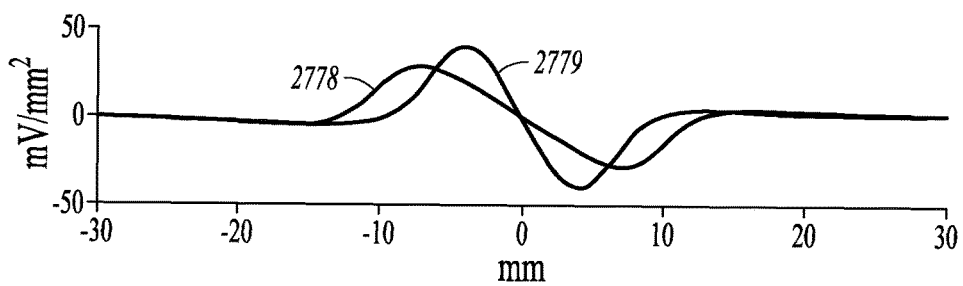
FIG. 27E compares a target multipole voltage per distance squared and a bipole voltage per distance squared (activating function).

FIG. 27E compares a target multipole voltage per distance squared 2778 (second order derivative of the voltage along the fiber axis) in mV per mm$^2$ for the base field design illustrated in FIG. 27A and a bipole voltage per distance squared 2779 (second order derivative of the voltage along the fiber axis) in mV per mm$^2$ for the traditional bipole illustrated in FIG. 27B. As illustrated in FIG. 27E, the target multipole voltage per distance squared 2778 has a smaller voltage amplitude bipole voltage per distance 2779 but also has a wider field. Thus, the base field design reduces the second order derivative of the voltage along the fiber axis. As stated previously, DC fibers have an activating function proportional to the second order derivative of the voltage along the fiber axis, so it is desirable to decrease the second order derivative of the voltage along the fiber axis to avoid modulation of DC fibers.

The field design may be applied to any frequency and to any amplitude. For example, the field design may be implemented for sub-perception modulation and may be implemented for supra-perception modulation.

Figures 28, 29:
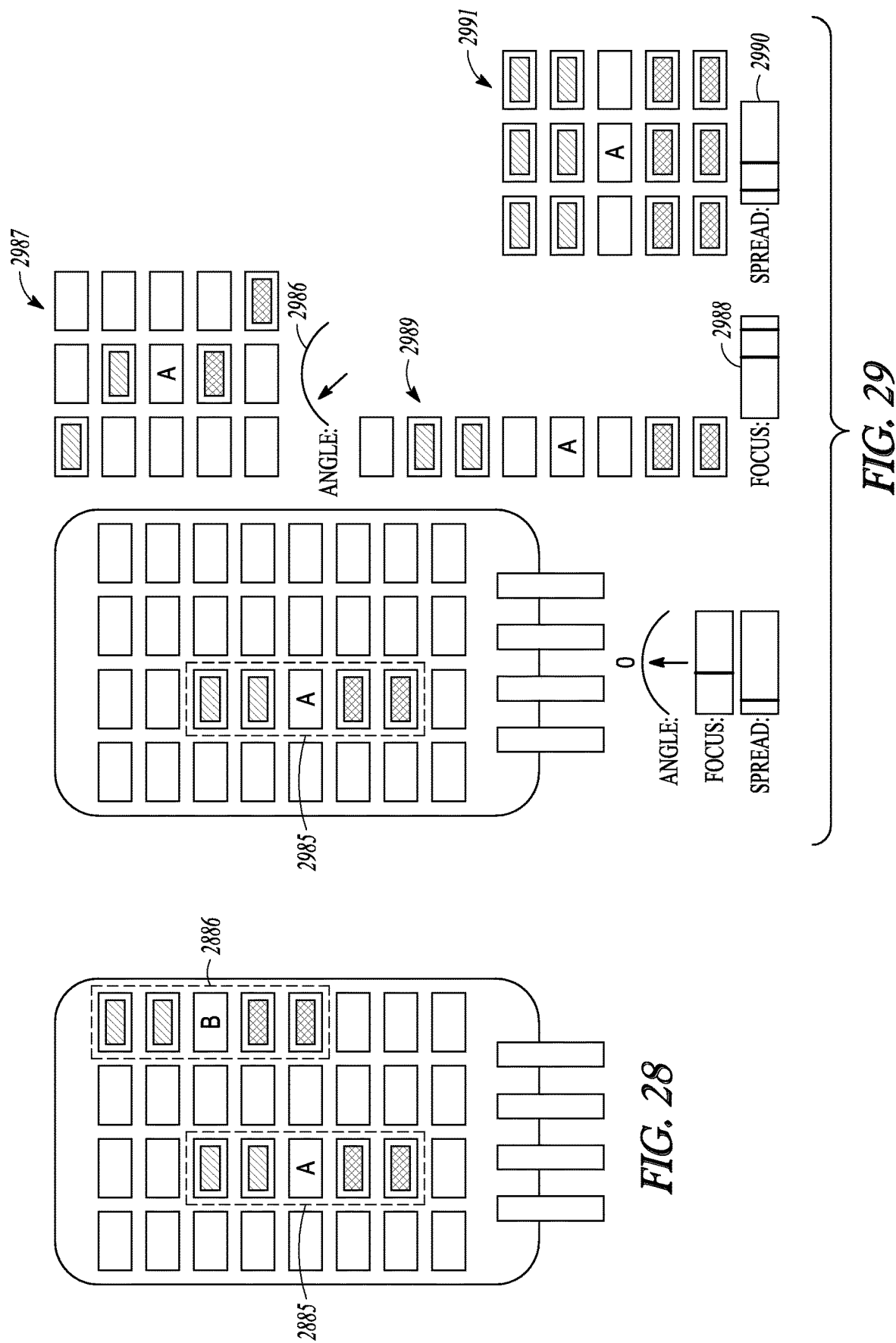
FIG. 28 illustrates an example, using a paddle lead, where a central point of stimulation (e.g. A) is identified, and a linear field may be centered around the central point of stimulation.
FIG. 29 illustrates, by way of example, advanced controls that may be implemented within a base field design interface.

FIG. 28 illustrates an example, using a paddle lead, where a central point of stimulation (e.g. A) is identified, and a linear field may be centered around the central point of stimulation. The centering of the linear field may be pre-programmed or may be calculated using a mathematical algorithm such as a forward/inverse solution paradigm. Multiple areas (e.g. "B") can be assigned simultaneously. Thus, in the illustrated example, there are a first target multipole 2885 and a second target multipole 2886 on the paddle lead. Each sweet spot can be tied to an "area" and linked to an independent timing source. Some embodiments may implement auto-controls, which may involve calculation of fields using offline software (e.g. COMSOL, MATLAB) and forward/inverse modeling to generate configuration that best matches target field specified/drawn by user.

FIG. 29 illustrates, by way of example and not limitation, advanced controls that may be implemented within a base field design interface. More advanced control allows the user to use settings in software suite (e.g. "Angle", "Focus", "Spread") to control angle orientation, vertical width, and horizontal width, respectively, of the linear field generated by the target multipole 2985 associated with the base field design. A paddle lead is illustrated with a central point of stimulation "A". Some interface embodiments provide an angle adjustment which can be controlled as illustrated at 2886 to allow a user to input an orientation for the base field design as illustrated at 2987. The angle adjustment could produce least-squares-error minimized fields that include more than two target anode and two target cathodes whose fractionalization assignments may differ from the base field embodiment with a fractionalization of 67/33/0/−33/−67 denoted earlier. Some interface embodiments provide a focus adjustment which can be controlled as illustrated at 2988 to change the distance of the target anode(s) and target cathode(s) from the central point of stimulation "A", which changes the extent of the electrical field along the orientation of the base field design as illustrated at 2989. Some interface embodiments provide a spread adjustment which can be controlled as illustrated at 2990, which changes the width or spread of the base field along a direction perpendicular to the orientation of the base field design as illustrated at 2991. The fractionalizations approximate the base field and may be pre-calculated for a given setting and/or calculated on-board. Some interface embodiments provide blended settings (e.g. angle+spread). Some interface embodiments provide an indication of the fractionalizations. Thus, the programming system may include a user interface configured to receive at least one user input selected from the group of user inputs consisting of a user input to adjust an angle of an axis of linear progression for the target multipole, a user input to adjust a focus of the target multipole to change a length of the linear electric field, and a user input to adjust a spread of the target multipole to change a width of the linear electric field.

Figure 30:
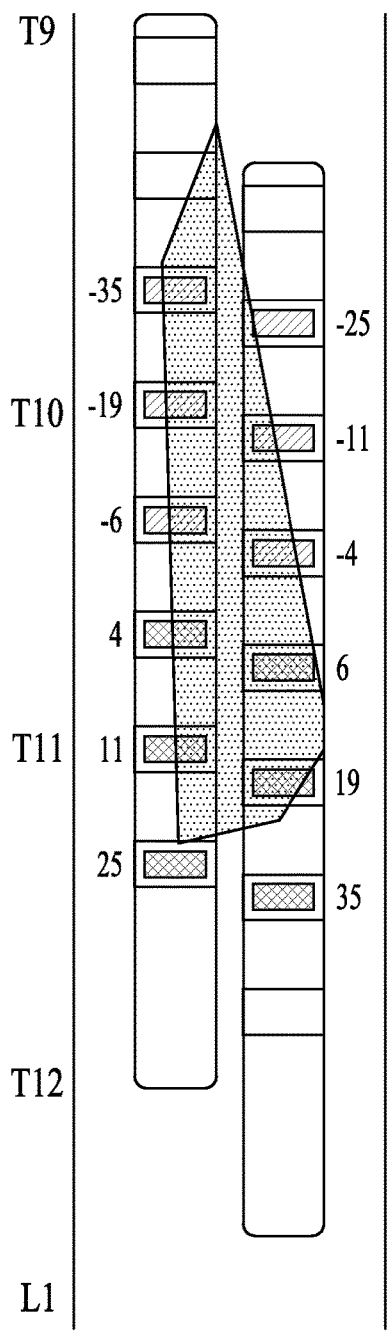
FIG. 30 illustrates a region drawn over a representation of electrodes implanted in a patient.
Figure 31:
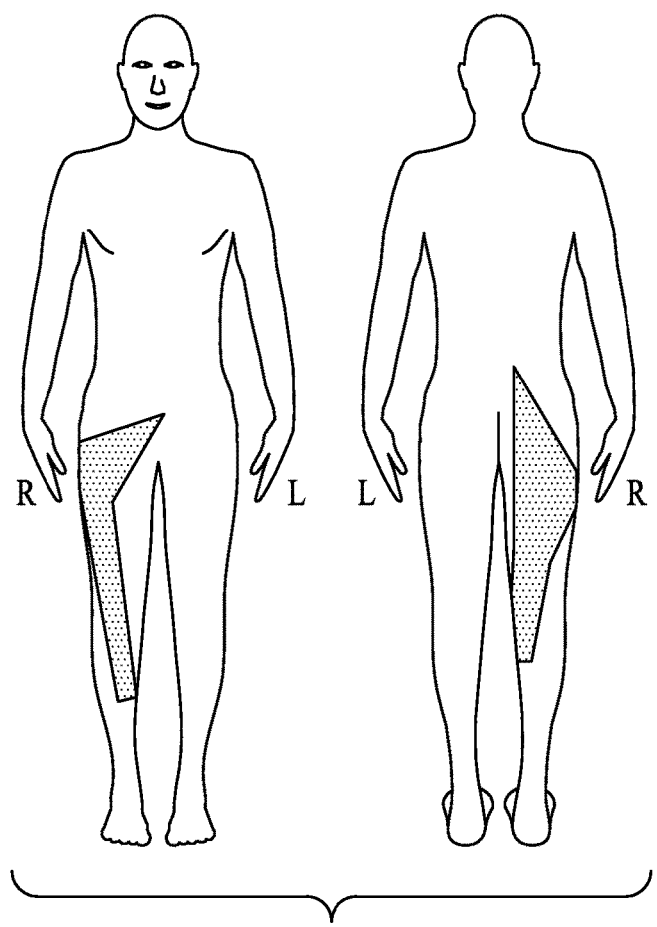
FIG. 31 illustrates a patient pain drawing which may serve as an input into the system for use in automatically or semi-automatically calculating the fractionalizations to provide a linear field to treat the pain in the identified regions.

FIGS. 30-31 illustrate, by way of example and not limitation, an example of features of an interface to enable anatomical and patient-guided targeting. The anatomical target may be drawn, may be derived from a patient pain drawing via a look up table or an algorithm, or may be a combination thereof. FIG. 30 illustrates a region drawn over a representation of electrodes implanted in a patient. The system may use the drawing of the region to automatically or semi-automatically calculate the fractionalizations to provide a linear field that proximate the base field over the region. The programming system may be configured to receive as a user input a user-drawn region on an anatomical representation, and automatically determine the target multipole based on the user input. The target multipole may be used to determine the electrode fractionalizations for the plurality of electrodes. FIG. 31 illustrates a patient pain drawing which may serve as an input into the system for use in automatically or semi-automatically calculating the fractionalizations to provide a linear field to treat the pain in the identified regions. Spatial location(s) on the patient may be mapped to specific dermatomal levels of the spinal cord and specific medial-lateral locations at a given level. The mapping may be a point-by-point mapping via a look-up table or a dictionary/key system. The center, length, and width of the target linear field may be determined based on the spatial extent of the spinal cord region corresponding to the patient's reported pain region. A clinician or other specialist, a patient or a combination of persons may work together to highlight region of spinal cord and/or body where they want stimulation to be targeted (i.e. focus stimulation on anatomical correlate and/or reported site of pain). Internal look-up table and/or inverse algorithm with field "primitives" tied to specific regions/region sizes may be used to display and configure electrode settings according to this anatomically-based specification. The programming system may be configured to receive as a user input a user-identified patient pain areas, and automatically determining the target multipole based on the user input. The target multipole may be used to determine the electrode fractionalizations for the plurality of electrodes.

Figures 32A, 32B, 32C, 32D, 32E, 32F:
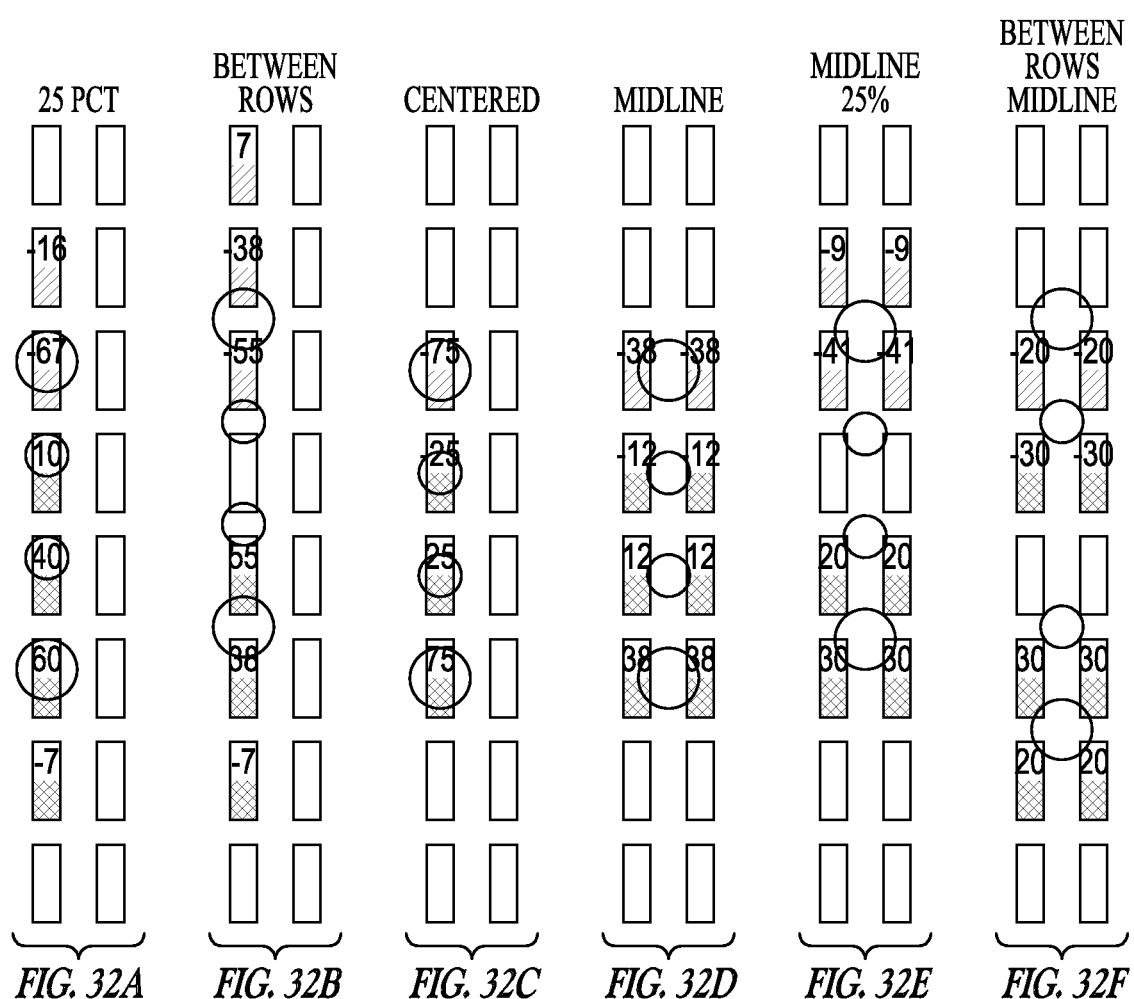
FIGS. 32A-32F generally illustrate the same target multipole with first and second target anodes and first and second target cathodes.

FIGS. 32A-32F generally illustrate the same target multipole with first and second target anodes and first and second target cathodes. The second target anode is larger than the first target anode, and the second target cathode is larger than the first target cathode. The fractionalized current delivered to the underlying physical electrodes may be adjusted to move the target multipole, by way of example and not limitation, to be centered laterally on the left column of electrodes with the target poles centered longitudinally at 25% from the electrode top (FIG. 32A), to be centered laterally on the left column of electrodes with the target poles centered longitudinally between rows in the left column of electrodes (FIG. 32B), to be centered laterally on the left column of electrodes with the target poles centered longitudinally on electrodes in the left column of electrodes (FIG. 32C), to be centered laterally on a midline between the columns and centered longitudinally with electrode rows (FIG. 32D), to be centered laterally on a midline between the columns with the target poles centered longitudinally at 25% from the electrode row top (FIG. 32E), and to be centered laterally on a midline between the columns with the target poles centered longitudinally between rows of electrodes (FIG. 32F).

Various embodiments disclosed herein may be implemented using a computer system, within which a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a personal computer (PC), a tablet PC, a hybrid tablet, a personal digital assistant (PDA), a mobile telephone, an implantable pulse generator (IPG), an external remote control (RC), a User's Programmer (CP), or any machine capable of executing instructions (sequential or otherwise) that specify actions to be taken by that machine. Further, the term "machine" shall also be taken to include any collection of machines that individually or jointly execute a set (or multiple sets) of instructions to perform any one or more of the methodologies discussed herein. One or more machines that are controlled by or operated by one or more processors (e.g., a computer) to individually or jointly execute instructions to perform any one or more of the methodologies discussed herein.

An example of a computer system includes at least one processor (e.g., a central processing unit (CPU), a graphics processing unit (GPU) or both, processor cores, compute nodes, etc.), a main memory and a static memory, which communicate with each other via a link (e.g., bus). The computer system may further include a video display unit, an alphanumeric input device (e.g., a keyboard), and a user interface (UI) navigation device (e.g., a mouse). In one embodiment, the video display unit, input device and UI navigation device are incorporated into a touch screen display. The computer system may additionally include a storage device (e.g., a drive unit), a signal generation device (e.g., a speaker), a network interface device, and one or more sensors (not shown), such as a global positioning system (GPS) sensor, compass, accelerometer, or other sensor. It will be understood that other forms of machines or apparatuses (such as IPG, RC, CP devices, and the like) that are capable of implementing the methodologies discussed in this disclosure may not incorporate or utilize every one of these components (such as a GPU, video display unit, keyboard, etc.). The storage device may include a machine-readable medium on which is stored one or more sets of data structures and instructions (e.g., software) embodying or utilized by any one or more of the methodologies or functions described herein. The instructions may also reside, completely or at least partially, within the main memory, static memory, and/or within the processor during execution thereof by the computer system, with the main memory, static memory, and the processor also constituting machine-readable media. While the machine-readable medium is illustrated in an example embodiment to be a single medium, the term "machine-readable medium" may include a single medium or multiple media (e.g., a centralized or distributed database, and/or associated caches and servers) that store the one or more instructions. The term "machine-readable medium" shall also be taken to include any tangible (e.g., non-transitory) medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks. The instructions may further be transmitted or received over a communications network using a transmission medium via the network interface device utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., Wi-Fi, 3G, and 4G LTE/LTE-A or 5G networks). The term "transmission medium" shall be taken to include any intangible medium that is capable of storing, encoding, or carrying instructions for execution by the machine, and includes digital or analog communications signals or other intangible medium to facilitate communication of such software.

The above detailed description is intended to be illustrative, and not restrictive. The scope of the disclosure should, therefore, be determined with references to the appended claims, along with the full scope of equivalents to which such claims are entitled.

What is claimed is:

1. A method performed using a neuromodulation device connected to at least one neuromodulation lead and configured to deliver neuromodulation energy to spinal cord tissue in a patient using the at least one neuromodulation lead, at least one processor, and at least one bilateral sensor having bilaterally-positioned neurophysiological sensors, the at least one bilateral sensor being configured to sense at least one neurophysiological signal on a right side of the patient and sense at least one neurophysiological signal of a left side of the patient to provide bilateral sensing data, wherein the method comprises automatically performing an objective calibration of at least a first electrode contact and a second electrode contact on the least one neuromodulation lead, wherein the automatically performing the objective calibration includes using the at least one processor to:
   instruct the neuromodulation device to deliver neuromodulation energy using at least the first electrode contact to cause a first neurophysiological response and using at least the second electrode contact of the lead to cause a second neurophysiological response;
   receive from the at least one bilateral sensor first bilateral sensed data corresponding to the first neurophysiological response and second bilateral sensed data corresponding to the sensed neurophysiological response;
   determine first neurophysiological response data based on the received first bilateral sensed data and determine second neurophysiological response data based on the received second bilateral sensed data, wherein the first and second neurophysiological response data include onset and amplitude; and
   determine 3D-related information, for input into a 3D programming algorithm, based on the first and second neurophysiological response data, wherein the 3D-related information include both:
      physiological midline information indicative of a medial-lateral position of the at least first electrode contact to the physiological midline and the at least second electrode contact to the physiological midline; and
      electrode-tissue coupling information indicative of a distance between the at least first electrode contact to the spinal cord tissue and a distance between the at least second electrode contact to the spinal cord tissue.

2. The method of claim 1, wherein the at least one bilateral sensor includes at least one bilateral sensor configured to bilaterally sense electromyograms (EMGs).

3. The method of claim 2, wherein the at least one bilateral sensor includes a plurality of EMG patches bilaterally positioned on the patient.

4. The method of claim 1, wherein the at least one bilateral sensor includes at least one bilateral sensor configured to bilaterally sense evoked compound action potentials (ECAPs).

5. The method of claim 4, wherein the at least one bilateral sensor includes an electrode contact on the neurostimulation lead other than an electrode contact being used to concurrently deliver neural modulation energy.

6. The method of claim 1, wherein the at least one bilateral sensor includes at least one bilateral sensor configured to bilaterally sense electroencephalograms (EEGs).

7. The method of claim 1, wherein the at least one bilateral sensor includes at least one bilateral sensor configured to bilaterally sense physiological signals indicative of changes in muscle tissue when the neural modulation energy is being delivered to provide bilateral sensing data.

8. The method of claim 1, wherein the method further comprises using the at least one processor to program the neuromodulator device using the 3D-programming algorithm and the physiological midline information and the electrode-tissue coupling information.

9. The method of claim 1, further comprising using the at least one processor to communicate the physiological midline information to a user interface to display a position of the at least one lead along with a representation of the physiological midline.

10. The method of claim 1, wherein the 3D-programming algorithm is configured use the physiological midline information and the electrode-tissue coupling information to determine fractionalized energy contribution of active electrodes on the at least one lead to create a stimulation field for a three-dimensional environment, wherein the determined fractionalized energy contribution includes a polarity for each of the active electrodes and a percentage of the energy contribution at the polarity for each of the active electrodes.

11. The method of claim 1, wherein performing the objective calibration of the at least the first electrode contact and the second electrode contact on the least one neuromodulation lead includes calibrating a plurality of electrode contacts on the neuromodulation lead, the method further including using the at least one processor to determine physiological midline information and electrode-tissue coupling information for each of the plurality of electrode contacts by instructing the neuromodulation device to step through a routine to deliver neuromodulation energy to cause a plurality of neurophysiological responses such that each of the plurality of electrode contacts is associated with at least one of the neurophysiological responses.

12. The method of claim 1, wherein:
performing the objective calibration of the at least the first electrode contact and the second electrode contact on the at least one neuromodulation lead includes calibrating less than all of a plurality of contacts on the at least one neuromodulation lead, including using the at least one processor to determine physiological midline information and electrode-tissue coupling information for a first subset of the plurality of electrode contacts by instructing the neuromodulation device to step through a routine to deliver neuromodulation energy to cause a plurality of neurophysiological responses, each of the first subset of the plurality of electrode contacts being associated with at least one of the plurality of neurophysiological responses, and each of a second subset of the plurality of electrode contacts being not associated with at least one of the neurophysiological responses, and
the method further comprises using the at least one processor to estimate at least one of the physiological midline information or the electrode-tissue coupling information for the second subset of the plurality of electrode contacts based on the determined physiological midline information and the electrode-tissue coupling information for the first subset of the plurality of electrode contacts.

13. The method of claim 1, wherein:
performing the objective calibration of the at least a first electrode contact and the second electrode contact on the least one neuromodulation lead includes instructing the neuromodulation device to deliver neuromodulation energy using at least a first neuromodulation parameter set and a second neuromodulation parameter set;
a neuromodulation parameter has a first value in the first neuromodulation parameter set and a second value in the second neuromodulation parameters set; and using the at least one processor to determine physiological midline information and electrode-tissue coupling information for the at least the first and second neuromodulation parameter sets.

14. The method of claim 13, further comprising using the at least one processor to interpolate at least one of the physiological midline information or the electrode-tissue coupling information for a neuromodulation parameter value based on at least the first value and the second value.

15. A non-transitory machine-readable medium including instructions, which when executed by a machine, cause the machine to automatically perform an objective calibration of at least a first electrode contact and a second electrode contact on at least one neuromodulation lead, including:
instruct a neuromodulation device to deliver neuromodulation energy using at least the first electrode contact to cause a first neurophysiological response and using at least the second electrode contact of the lead to cause a second neurophysiological response;
receive from at least one bilateral sensor first bilateral sensed data corresponding to the first neurophysiological response and second bilateral sensed data corresponding to the sensed neurophysiological response, wherein the at least one bilateral sensor has bilaterally-positioned neurophysiological sensors and is configured to sense at least one neurophysiological signal on a right side of the patient and sense at least one neurophysiological signal on a left side of the patient to provide each of the first and second bilateral sensed data;
determine first neurophysiological response data based on the received first bilateral sensed data and determine second neurophysiological response data based on the received second bilateral sensed data, wherein the first and second neurophysiological response data include onset and amplitude; and
determine 3D-related information, for input into a 3D programming algorithm, based on the first and second neurophysiological response data, wherein the 3D-related information include both:
physiological midline information indicative of a medial-lateral position of the at least first electrode contact to the physiological midline and the at least second electrode contact to the physiological midline; and
electrode-tissue coupling information indicative of a distance between the at least first electrode contact to the spinal cord tissue and a distance between the at least second electrode contact to the spinal cord tissue.

16. The non-transitory machine-readable medium of claim 15, wherein the instructions, which when executed by the machine, cause the machine to program the neuromodulator device using the physiological midline information and the electrode-tissue coupling information.

17. The non-transitory machine-readable medium of claim 15, wherein the instructions, which when executed by the machine, cause the machine to communicate the physiological midline information to a user interface to display a position of the at least one lead along with a representation of the physiological midline.

18. The non-transitory machine-readable medium of claim 15, wherein the 3D-programming algorithm is configured use the physiological midline information and the electrode-tissue coupling information to determine fractionalized energy contribution of active electrodes on the at least one lead to create a stimulation field for a three-dimensional environment, wherein the determined fractionalized energy contribution includes a polarity for each of the active electrodes and a percentage of the energy contribution at the polarity for each of the active electrodes.

19. A system configured for use with a neuromodulation device connected to at least one neuromodulation lead, wherein the neuromodulation device is configured to deliver neuromodulation energy to spinal cord tissue in a patient using the at least one neuromodulation lead, the system including:
- at least one bilateral sensor, having bilaterally-positioned neurophysiological sensors, configured to sense at least one neurophysiological signal on a right side of the patient and sense at least one neurophysiological signal of a left side of the patient to provide bilateral sensing data; and
- at least one processor configured to automatically perform an objective calibration of at least a first electrode contact and a second electrode contact on the least one neuromodulation lead, including:
  - instruct the neuromodulation device to deliver neuromodulation energy using at least the first electrode contact to cause a first neurophysiological response and using at least the second electrode contact of the lead to cause a second neurophysiological response;
  - receive from the at least one bilateral sensor first sensed data corresponding to the first neurophysiological response and second sensed data corresponding to the second neurophysiological response; and
  - determine 3D-related information, including onset and amplitude, based on the first and second neurophysiological responses for input into a 3D-programming algorithm, physiological midline information indicative of a medial-lateral position of the at least first electrode contact to the physiological midline and the at least second electrode contact to the physiological midline.

20. The system of claim 19, wherein the at least one bilateral sensor includes bilaterally-positioned electromyogram (EMG) sensors, bilaterally-positioned evoked compound action potential (ECAP) sensors, or bilaterally-positioned electroencephalogram (EEG) sensors.

* * * * *